United States Patent
Giencke et al.

(10) Patent No.: US 6,239,071 B1
(45) Date of Patent: *May 29, 2001

(54) 2,4-DIAMINO-1,3,5-TRIAZINES, PROCESSES FOR THEIR PREPARATION AND THEIR USE AS HERBICIDES AND PLANT GROWTH REGULATORS

(75) Inventors: Wolfgang Giencke, Hofheim; Klemens Minn, Hattersheim; Lothar Willms, Hofheim; Hermann Bieringer, Eppstein; Klaus Bauer, Hanau; Christopher Rosinger, Hofheim, all of (DE)

(73) Assignee: Hoecht Schering AgrEvo GmbH, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/701,360

(22) Filed: Aug. 22, 1996

(30) Foreign Application Priority Data

Aug. 24, 1995 (DE) .............................................. 195 31 084

(51) Int. Cl.[7] ........................ A01N 43/68; C07D 251/18; C07D 403/14
(52) U.S. Cl. ......................... 504/113; 504/234; 544/208; 544/209
(58) Field of Search ................................. 544/208, 209; 504/113, 234

(56) References Cited

U.S. PATENT DOCUMENTS

| | | |
|---|---|---|
| 3,758,471 | 9/1973 | Irikura et al. . |
| 3,816,419 | 6/1974 | Cross et al. ........................ 260/249.9 |
| 3,932,167 * | 1/1976 | Cross et al. ............................... 71/93 |
| 4,956,363 | 9/1990 | Wülfert et al. . |

FOREIGN PATENT DOCUMENTS

| | | |
|---|---|---|
| 0411153 | 2/1991 | (EP) . |
| 0 492 615 | 7/1992 | (EP) . |
| 0 509 544 | 10/1992 | (EP) . |
| 88/02368 | 4/1988 | (WO) . |
| 90/09373 | 8/1990 | (WO) . |
| 94/24086 | 10/1994 | (WO) . |
| WO 95/06642 | 3/1995 | (WO) . |

OTHER PUBLICATIONS

Database WPI Section Ch. Week 7746, Derwent Publications Ltd., London, DB, AN 77–81704Y.

Chemical Abstracts, vol. 110, No. 13, Mar. 27, 1989, Abstract No. 114801 by Kelarev et al. entitled "Synthesis and properties of sym–triazine derivatives. 8. Synthesis of amino–and alkoxy–substituted sym–triazines containing fragments of sterically hindered phenol starting from 2,4–bis(trichloromethyl)–sym–triazines".

Chemical Abstracts, vol. 086, No. 7, Feb. 14, 1977, Abstract No. 037551 by A. Tobe entitled "Pharmacological studies of triazine derivatives. I. General pharmacological actions".

Chemical Abstracts, vol. 090, No. 3, Jan. 15, 1979, Abstract No. 022979 by J. Sluka et al. entitled "2,4–Diamino–6–phenyl–1,3,5–triazines".

Chemical Abstracts, vol. 089, No. 5, Jul. 31, 1978, Abstract No. 043338 by Sciortino et al. entitled New substituted s–triazine of possible pharmacological interest.

Chemical Abstracts, vol. 088, No. 17, Apr. 24, 1978, Abstract No. 121115 by Ovsepyan et al. entitled "Synthesis and mutagenic action of 6–chloromethyl, cyanomethyl, and beta–aminoethyl derivatives of substituted 1,3,5–traizines".

Chemical Abstracts. vol. 079, No. 17, Oct. 29, 1973, Abstract No. 105207 by M.V. Guioca entitled New substituted triazines and their diuretic activity.

Chemical Abstracts, vol. 079, No. 15, Oct. 15, 1973, Abstract No. 092165 by A. Colautti et al. entitled substituted s–triazines and amidinoureas of potential pharmacological activity.

* cited by examiner

*Primary Examiner*—Mukund J. Shah
*Assistant Examiner*—Bruck Kifle
(74) *Attorney, Agent, or Firm*—Frommer Lawrence & Haug LLP

(57) ABSTRACT

Compounds of the formula (I) and their salts

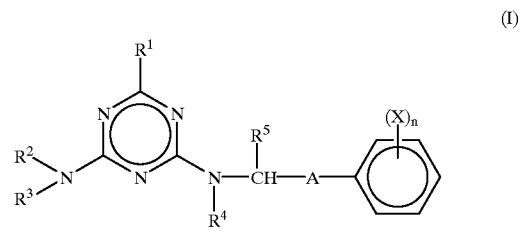

(I)

in which $R^1$ is optionally substituted ($C_1$–$C_6$)alkyl or optionally substituted phenyl, A is an optionally substituted hydrocarbon diradical and $R^2$, $R^3$, $R^4$, $R^5$, X and n are as defined in claim 1, are suitable as herbicides and plant growth regulators. The compounds (I) can be prepared according to processes as claimed in claim 6 by means of intermediates which are novel in some cases, e.g. of the formula (IV) as claimed in claim 10.

9 Claims, No Drawings

2,4-DIAMINO-1,3,5-TRIAZINES, PROCESSES FOR THEIR PREPARATION AND THEIR USE AS HERBICIDES AND PLANT GROWTH REGULATORS

The invention relates to the technical field of herbicides and plant growth regulators, in particular of herbicides for the selective control of weeds and grass weeds in crops of useful plants.

It has been disclosed that 2-amino-4-(phenoxyalkylamino)-1,3,5-triazines substituted in the 6-position have herbicidal and plant growth-regulating properties; cf. WO 94/24086, EP-A-509544, EP-A-492,615. Furthermore, 2-amino-4-[arylamino- or (hetero) arylalkylamino]-6-haloalkyl-1,3,5-triazines having herbicidal action have already been disclosed; cf. U.S. Pat. No. 3,816,419, WO 90/09378, WO 88/02368.

The known active compounds having a 4-[(hetero) arylalkylamino] group in this case each contain a methylene bridge as "alkyl", which is optionally additionally branch-substituted.

The known active compounds in some cases have disadvantages in their use, be it inadequate herbicidal action against harmful plants, too narrow a spectrum of harmful plants which can be controlled using an active compound, or too low a selectivity in crops of useful plants. Other active compounds cannot be prepared economically on the industrial scale because of poorly accessible precursors and reagents or only have inadequate chemical stabilities.

It is an object of the invention to provide alternative active compounds of the 2,4-diamino-1,3,5-triazines type, which can be employed as herbicides or plant growth regulators.

In German Patent Application No. 19 522 137.0, herbicides of the type mentioned, inter alia, are proposed which in the 6-position on the triazine ring contain an optionally substituted cycloalkyl radical or a heterocycle having an oxygen, nitrogen or sulfur atom and in the 4-position have a phenylalkyl radical having a linear propylene bridge which is optionally additionally branch-substituted.

The present invention relates to compounds of the formula I and their salts

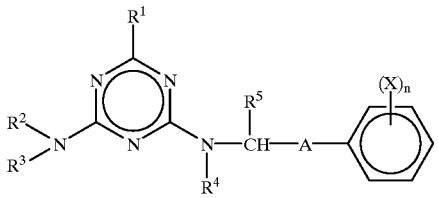

(I)

in which $R^1$ is $(C_1-C_6)$alkyl, which is unsubstituted or substituted by one or more radicals from the group consisting of halogen, cyano, nitro, thiocyanato, $(C_1-C_4)$alkoxy, $(C_1-C_4)$alkylthio, $(C_1-C_4)$alkylsulfinyl, $(C_1-C_4)$alkylsulfonyl, $(C_2-C_4)$alkenyl, $(C_2-C_4)$alkynyl, $(C_3-C_9)$cycloalkyl which is unsubstituted or substituted, and phenyl which is unsubstituted or substituted, and heterocyclyl having 3 to 6 ring atoms and 1 to 3 hetero ring atoms from the group consisting of N, O and S, the ring being unsubstituted or substituted, or phenyl which is unsubstituted or substituted, $R^2$ and $R^3$ each independently of one another are hydrogen, amino or alkylamino or dialkylamino each having 1 to 6 carbon atoms in the alkyl radical, an acyclic or cyclic hydrocarbon radical or hydrocarbon-oxy radical each having 1 to 10 carbon atoms, preferably having 1 to 6 carbon atoms, or a heterocyclyl radical, heterocyclyloxy radical or heterocyclylamino radical each having 3 to 6 ring atoms and 1 to 3 hetero ring atoms from the group consisting of N, O and S, each of the five last mentioned radicals being unsubstituted or substituted, or an acyl radical, or $R^2$ and $R^3$ together with the nitrogen atom of the group $NR^2R^3$ are a heterocyclic radical having 3 to 6 ring atoms and 1 to 4 hetero ring atoms, in addition to the nitrogen atom the possible further hetero ring atoms being selected from the group consisting of N, O and S and the radical being unsubstituted or substituted, $R^4$ is hydrogen, amino, alkylamino or dialkylamino each having 1 to 6 carbon atoms in the alkyl radical, an acyclic or cyclic hydrocarbon radical or hydrocarbon-oxy radical each having 1 to 10 carbon atoms, preferably having 1 to 6 carbon atoms, or a heterocyclyl radical, heterocyclyloxy radical or heterocyclylamino radical each having 3 to 6 ring atoms and 1 to 3 hetero ring atoms from the group consisting of N, O and S, each of the five last mentioned radicals being unsubstituted or substituted, or an acyl radical, $R^5$ is hydrogen, halogen, nitro, cyano, thiocyanato or a radical of the formula $-B^1-Y^1$, $B^1$ and $Y^1$ being as defined below, A is an alkylene radical having 1 to 5 linearly linked carbon atoms or alkenylene or alkynylene each having 2 to 5 linearly linked carbon atoms, each of the three last mentioned diradicals being unsubstituted or substituted by one or more radicals from the group consisting of halogen, nitro, cyano, thiocyanato and a radical of the formula $-B^2-Y^2$, $(X)_n$ is n substituents X and in this case X in each case independently of one another is halogen, OH, $NH_2$, $NO_2$, CHO, COOH, CN, SCN or a radical of the formula $-B^0-R$, $B^0$ being as defined below and R being an acyclic hydrocarbon radical having 1 to 6 carbon atoms, which is unsubstituted or substituted, or a radical of the formula $-B^0-R^0$, $B^0$ being as defined below and $R^0$ being an aromatic, saturated or partially saturated carbocyclic or heterocyclic radical, the cyclic radical being substituted or unsubstituted, or two adjacent radicals X together are a fused cyclic system having 4 to 6 ring atoms, which is carbocyclic or contains hetero ring atoms from the group consisting of O, S and N and which is unsubstituted or substituted by one or more radicals from the group consisting of halogen, $(C_1-C_4)$alkyl and oxo, preferably X in each case independently of one another is halogen, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_1-C_6)$alkylthio, $[(C_1-C_4)$alkyl]carbonyl, $[(C_1-C_4)$alkoxy]carbonyl or $[(C_1-C_4)$alkylthio]carbonyl, the hydrocarbon-containing moieties in the last mentioned 9 radicals being unsubstituted or substituted, n is 0, 1, 2, 3, 4 or 5, preferably 0, 1, 2, 3 or 4, in particular 2 or 3, $B^0, B^1, B^2$ in each case independently of one another are a direct bond or a divalent group of the formula $-O-$, $-S(O)_p-$, $-S(O)_p-O-$, $-O-S(O)_p-$, $-CO-$, $-O-CO-$, $-CO-O-$, $-S-CO-$, $-CO-S-$, $-S-CS-$, $-CS-S-$, $-O-CO-O-$, $-NR'-$, $-O-NR'-$, $-NR'-O-$, $-NR'-CO-$, $-CO-NR'-$, $-O-CO-NR'-$, $-NR'-CO-O-$ or $-NR'-CO-NR''-$, where p=0, 1 or 2 and R' and R'' independently of one another are hydrogen, alkyl having 1 to 6 carbon atoms, phenyl, benzyl, cycloalkyl having 3 to 6 carbon atoms or alkanoyl having 1 to 6 carbon atoms, $Y^1, Y^2$ each independently of one another are H or an acyclic hydrocarbon radical, for example having 1 to 20 carbon atoms, preferably having 1 to 10 carbon atoms, or a cyclic hydrocarbon radical having 3 to 8 carbon atoms, preferably 3 to 6 carbon atoms, or a heterocyclic radical having 3 to 9 ring atoms and 1 to 3 hetero ring atoms from the group consisting of N, O and S, each of the three last mentioned radicals being unsubstituted or substituted.

The compounds of the formula (I) can form salts by addition of a suitable inorganic or organic acid, such as, for example, HCl, HBr, $H_2SO_4$ or $HNO_3$, but also oxalic acid or sulfonic acids, to a basic group, such as, for example, amino or alkylamino. Suitable substituents which are present in deprotonated form, such as, for example, sulfonic acids or carboxylic acids, can form internal salts with groups which, for their part, can be protonated, such as amino groups. Salts can likewise be formed by replacing the hydrogen in suitable substituents, such as, for example, sulfonic acids or carboxylic acids, by a cation which is suitable for agriculture. These salts are, for example, metal salts, in particular alkali metal salts or alkaline earth metal salts, in particular sodium and potassium salts, or alternatively ammonium salts or salts with organic amines.

In formula (I) and all following formulae, the radicals alkyl, alkoxy, haloalkyl, haloalkoxy, alkylamino and alkylthio and also the corresponding unsaturated and/or substituted radicals in the hydrocarbon structure can each be straight-chain or branched. If not specifically stated, in these radicals the lower hydrocarbon structures, e.g. having 1 to 6 carbon atoms or, in unsaturated groups, having 2 to 6 carbon atoms, are preferred. Alkyl radicals, even in the combined meanings such as alkoxy, haloalkyl etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the possible unsaturated radicals corresponding to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl; alkynyl is, for example, propargyl, but-2-yn-1-yl, but-3-yn-1-yl or 1-methyl-but-3-yn-1-yl.

Cycloalkyl is a carbocyclic, saturated ring system preferably having 3–8 carbon atoms, e.g. cyclopropyl, cyclopentyl or cyclohexyl.

Halogen is, for example, fluorine, chlorine, bromine or iodine. Haloalkyl, -alkenyl and -alkynyl are alkyl, alkenyl or alkynyl partially or completely substituted by halogen, preferably by fluorine, chlorine and/or bromine, in particular by fluorine or chlorine, e.g. monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies to haloalkenyl and other radicals substituted by halogen.

A hydrocarbon radical is a straight-chain, branched or cyclic and saturated or unsaturated aliphatic or aromatic hydrocarbon radical, e.g. alkyl, alkenyl, alkynyl, cycloalkyl, cycloalkenyl or aryl; aryl is in this case a mono-, bi- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5, 6 or 7 ring atoms or phenyl; the same applies to a hydrocarbon radical in a hydrocarbon-oxy radical.

A heterocyclic radical or ring (heterocyclyl) can be saturated, unsaturated or heteroaromatic; it preferably contains one or more hetero units in the ring, i.e. heteroatoms or ring members which also include substituted heteroatoms, preferably from the group consisting of N, O, S, SO, $SO_2$; preferably it is an aliphatic heterocyclyl radical having 3 to 7 ring atoms or a heteroaromatic radical having 5 or 6 ring atoms and contains 1, 2 or 3 hetero units. The heterocyclic radical can, for example, be a heteroaromatic radical or ring (heteroaryl), such as, for example, a mono-, bi- or polycyclic aromatic system in which at least 1 ring contains one or more heteroatoms, for example pyridyl, pyrimidinyl, pyridazinyl, pyrazinyl, thienyl, thiazolyl, oxazolyl, furyl, pyrrolyl, pyrazolyl and imidazolyl, or is a partially or completely hydrogenated radical such as oxiranyl, pyrrolidyl, piperidyl, piperazinyl, dioxolanyl, morpholinyl or tetrahydrofuryl. Possible substituents for a substituted heterocyclic radical are the substituents mentioned further below, and additionally also oxo. The oxo group can also occur on the hetero ring atoms, which can exist in various oxidation states, e.g. in the case of N and S.

Substituted radicals, such as substituted hydrocarbon radicals, e.g. substituted alkyl, alkenyl, alkynyl, aryl, phenyl and benzyl, or substituted heterocyclyl or heteroaryl, are, for example, a substituted radical derived from the unsubstituted parent substance, the substituents being, for example, one or more, preferably 1, 2 or 3, radicals from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl; the term "substituted radicals" such as substituted alkyl etc. includes as substituents, additionally to the saturated hydrocarbon-containing radicals mentioned, corresponding unsaturated aliphatic and aromatic radicals, such as optionally substituted alkenyl, alkynyl, alkenyloxy, alkynyloxy, phenyl, phenoxy etc. In the case of radicals having carbon atoms, those having 1 to 4 carbon atoms, in particular 1 or 2 carbon atoms, are preferred. Preferred substituents are, as a rule, those from the group consisting of halogen, e.g. fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy $(C_1-C_4)$haloalkoxy, nitro and cyano. Particularly preferred in this case are the substituents methyl, methoxy and chlorine.

Mono- or disubstituted amino is a chemically stable radical selected from the group of substituted amino radicals, which are N-substituted, for example, by one or two identical or different radicals from the group consisting of alkyl, alkoxy, acyl and aryl, preferably monoalkylamino, dialkylamino, acylamino, arylamino, N-alkyl-N-arylamino and also N-heterocycles; in this case alkyl radicals having 1 to 4 carbon atoms are preferred; aryl in this case is preferably phenyl or substituted phenyl; for acyl the definition mentioned further below applies, preferably $(C_1-C_4)$ alkanoyl. The same applies to substituted hydroxylamino or hydrazino.

Optionally substituted phenyl is preferably phenyl which is unsubstituted or mono- or polysubstituted, preferably up to trisubstituted, by identical or different radicals from the group consisting of halogen, $(C_1-C_4)$alkyl, $(C_1-C_4)$alkoxy, $(C_1-C_4)$haloalkyl, $(C_1-C_4)$haloalkoxy and nitro, e.g. o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is the radical of an organic acid, e.g. the radical of a carboxylic acid and radicals of acids derived therefrom such as thiocarboxylic acid, optionally N-substituted iminocarboxylic acids or the radical of carbonic acid monoesters, optionally N-substituted carbamic acid, sulfonic acids, sulfinic acids, phosphonic acids or phosphinic acids. Acyl is, for example, formyl, alkylcarbonyl such as [$(C_1-C_4)$alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. In this case the radicals can in each case be additionally substituted in the alkyl or phenyl moiety, for example in the alkyl moiety, by one or more radicals from the group consisting of halogen, alkoxy, phenyl and phenoxy; examples of substituents in the phenyl moiety are the substituents already generally mentioned further above for substituted phenyl.

The invention also relates to all stereoisomers which are embraced by formula (I), and their mixtures. Such compounds of the formula (I) contain one or more asymmetric carbon atoms or alternatively double bonds which are not separately indicated in the formula (I). The possible stereoisomers defined by their specific spatial form, such as enantiomers, diastereomers, Z- and E-isomers, are all embraced by the formula (I) and can be obtained from mixtures of the stereoisomers by customary methods or alternatively prepared by stereoselective reactions in combination with the use of stereochemically pure starting substances.

Especially for reasons of greater herbicidal action, better selectivity and/or better preparability, of particular interest are compounds of said formula (I) according to the invention or their salts in which $R^1$ is $(C_1-C_4)$alkyl, which is unsubstituted or substituted by one or more radicals from the group consisting of halogen, $(C_1-C_4)$alkoxy, $(C_1-C_4)$alkylthio, $(C_1-C_4)$alkylsulfonyl, $(C_3-C_9)$cycloalkyl which is unsubstituted or substituted, and phenyl which is unsubstituted or substituted by one or more radicals from the group consisting of halogen, $(C_1-C_4)$alkyl and $(C_1-C_4)$haloalkyl, $(C_1-C_4)$alkoxy, $(C_1-C_4)$haloalkoxy, $(C_1-C_4)$alkylthio, amino, mono- and di[$(C_1-C_4)$alkyl]amino, $(C_1-C_4)$alkanoylamino, benzoylamino, nitro, cyano, [$(C_1-C_4)$alkyl]carbonyl, formyl, carbamoyl, mono- and di-[$(C_1-C_4)$alkyl]aminocarbonyl and $(C_1-C_4)$alkylsulfonyl, and heterocyclyl having 3 to 6 ring atoms and 1 to 3 hetero ring atoms from the group consisting of N, O and S, the ring being unsubstituted or substituted by one or more radicals from the group consisting of halogen, $(C_1-C_4)$alkyl and oxo, or phenyl which is unsubstituted or substituted, $R^2$ and $R^3$ each independently of one another are hydrogen, amino or alkylamino or dialkylamino each having 1 to 4 carbon atoms in the alkyl radical, an acyclic or cyclic hydrocarbon radical or hydrocarbon-oxy radical each having 1 to 6 carbon atoms or a heterocyclyl radical, heterocyclyloxy radical or heterocyclylamino radical each having 3 to 6 ring atoms and 1 to 3 hetero ring atoms from the group consisting of N, O and S, each of the five last mentioned radicals being unsubstituted or substituted by one or more radicals from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, [$(C_1-C_4)$alkoxy]carbonyl, [$(C_1-C_4)$alkyl]carbonyl, formyl, carbamoyl, mono- and di-[$(C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, or an acyl radical or $R^2$ and $R^3$ together with the nitrogen atom of the group $NR^2R^3$ are a heterocyclic radical having 3 to 6 ring atoms and 1 to 2 hetero ring atoms, in addition to the nitrogen atom the possible further hetero ring atom being selected from the group consisting of N, O and S and the radical being unsubstituted or substituted by one or more radicals from the group consisting of halogen, $(C_1-C_4)$alkyl and oxo, $R^4$ is hydrogen, amino, alkylamino or dialkylamino each having 1 to 6 carbon atoms in the alkyl radical, an acyclic or cyclic hydrocarbon radical or hydrocarbon-oxy radical each having 1 to 6 carbon atoms or a heterocyclyl radical, heterocyclyloxy radical or heterocyclylamino radical each having 3 to 6 ring atoms and 1 to 3 hetero ring atoms from the group consisting of N, O and S, each of the five last mentioned radicals being unsubstituted or substituted by one or more radicals from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, [$(C_1-C_4)$alkoxy]carbonyl, [$(C_1-C_4)$alkyl]carbonyl, formyl, carbamoyl, mono- and di-[$(C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, or an acyl radical, $R^5$ is hydrogen, halogen or a radical of the formula $—B^1—Y^1$, $B^1$ and $Y^1$ being as defined below, A is a divalent radical of the formula $A^1$, $A^2$, $A^3$ or $A^4$

 (A$^1$)

 (A$^2$)

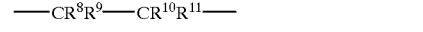 (A$^3$)

 (A$^4$)

$R^6, R^7, R^8, R^9, R^{10}, R^{11}, R^{12}, R^{13}, R^{14}, R^{15}, R^{16}, R^{17}, R^{18}$ and $R^{19}$ each independently of one another are halogen, nitro, cyano, thiocyanato or a radical of the formula $—B^2—Y^2$, $(X)_n$ is n substituents X and in this case X in each case independently of one another is halogen, OH, $NH_2$, $NO_2$, CHO, COOH, CN, SCN or a radical of the formula $—B^0—R^0$, $B^0$ being as defined below and $R^0$ being $(C_1-C_6)$alkyl, $(C_2-C_6)$alkenyl or $(C_2-C_6)$alkynyl, each of the 3 last mentioned radicals being unsubstituted or substituted, or a radical of the formula $—B^0—R^0$, $B^0$ being as defined below, and $R^0$ being $(C_3-C_6)$cycloalkyl, $(C_3-C_6)$cycloalkenyl or phenyl, each of the last mentioned three radicals being unsubstituted or substituted, preferably by one or more radicals from the group halogen, $(C_1-C_4)$alkyl, $(C_1-C_4)$haloalkyl and $(C_1-C_4)$alkoxy, or two adjacent radicals X together are a fused cyclic system having 4 to 6 ring atoms, which is carbocyclic or contains hetero ring atoms from the group consisting of O, S and N and which is unsubstituted or substituted by one or more radicals from the group consisting of halogen, $(C_1-C_4)$alkyl and oxo, preferably X in each case independently of one another is halogen, $(C_1-C_6)$alkyl, $(C_1-C_6)$alkoxy, $(C_1-C_4)$alkylcarbonyl, $(C_1-C_4)$alkyloxycarbonyl or $(C_1-C_4)$alkylthiocarbonyl, the last mentioned five radicals being unsubstituted or substituted by halogen or $(C_1-C_4)$alkoxy, n is 0, 1, 2, 3 or 4, preferably 2 or 3, $B^0, B^1, B^2$ each independently of one another are a direct bond or a divalent group of the formula —O—, —S—, —CO—, —O—CO—, —CO—O—, —S—CO—, —CO—S—, —O—CO—O—, —NR'—, —NR'—CO—, —CO—NR'—, —O—CO—NR'—, —NR'—CO—O— or —NR° CONR"—, R' and R" independently of one another being H or $(C_1-C_4)$alkyl, $Y^1, Y^2$ each independently of one another are H or an acyclic hydrocarbon radical having 1 to 6 carbon atoms, a cyclic hydrocarbon radical having 3 to 6 carbon atoms or a heterocyclic radical having 3 to 9 ring atoms and 1 to 3 hetero ring atoms from the group consisting of N, O and S, each of the three last mentioned radicals being unsubstituted or substituted by one or more radicals from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy]carbonyl, $[(C_1-C_4)$alkyl]carbonyl, formyl, carbamoyl, mono- and di-$[(C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl.

Of particular interest are furthermore compounds of the formula (I) according to the invention and their salts in which $R^1$ is $(C_1-C_4)$alkyl, which is unsubstituted or substituted by one or more radicals from the group consisting of halogen, $(C_1-C_4)$alkoxy, $(C_1-C_4)$alkylthio, $(C_3-C_6)$cycloalkyl, which is unsubstituted or substituted by one or more radicals from the group consisting of halogen, $(C_1-C_4)$alkyl, $(C_1-C_4)$haloalkyl, $(C_1-C_4)$alkoxy and $(C_1-C_4)$haloalkoxy, and phenyl which is unsubstituted or substituted by one or more radicals from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, nitro, cyano, $[(C_1-C_2)$alkyl]carbonyl, formyl, carbamoyl, mono- and di-$[(C_1-C_2)$alkyl]aminocarbonyl and $(C_1-C_4)$alkylsulfonyl, or phenyl which is unsubstituted or substituted by one or more radicals from the group consisting of halogen, $(C_1-C_4)$alkyl and $(C_1-C_4)$haloalkyl, $(C_1-C_4)$alkoxy, $(C_1-C_4)$haloalkoxy, $(C_1-C_4)$alkylthio, nitro, cyano, $[(C_1-C_2)$alkyl]carbonyl, formyl, carbamoyl, mono- and di-$[(C_1-C_2)$alkyl]aminocarbonyl and $(C_1-C_4)$alkylsulfonyl, $R^2$ and $R^3$ independently of one another are hydrogen, amino, formyl, $(C_1-C_4)$alkyl, cyano-$(C_1-C_4)$alkyl, $(C_1-C_4)$alkylamino, di-$[(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo$(C_1-C_4)$alkoxy-$(C_1-C_4)$alkyl, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di-$[(C_1-C_4)$alkyl]amino-$(C_1-C_4)$alkyl, $(C_3-C_9)$cycloalkylamino-$(C_1-C_4)$alkyl, $(C_3-C_9)$cycloalkyl, $(C_3-C_9)$heterocyclyl-$(C_1-C_4)$alkyl having 3 to 9 ring members, the cyclic groups in the last mentioned 3 radicals being unsubstituted or substituted by one or more, preferably up to three, radicals from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, aminocarbonyl, $(C_1-C_4)$alkylaminocarbonyl, phenoxy-$(C_1-C_4)$alkyl, phenyl-$(C_1-C_4)$alkyl, heterocyclyl, heterocyclylamino, heterocyclyloxy, heterocyclylthio, or one of the last mentioned 16 radicals, which is substituted in the acyclic moiety or, preferably, in the cyclic moiety by one or more radicals from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl, $(C_1-C_4)$alkoxy, heterocyclyl in the radicals in each case containing 3 to 9 ring atoms and 1 to 3 hetero ring atoms from the group consisting of N, O and S, or $R^2$ and $R^3$ together with the nitrogen atom of the group $NR^2R^3$ are a heterocyclic radical having 3 to 6 ring atoms and 1 to 2 hetero ring atoms, in addition to the nitrogen atom the possible further hetero ring atom being selected from the group consisting of N, O and S and the radical being unsubstituted or substituted by one or more radicals from the group consisting of halogen, $(C_1-C_4)$alkyl and oxo, $R^4$ is hydrogen, amino, formyl, $(C_1-C_4)$alkyl, cyano-$(C_1-C_4)$alkyl, $(C_1-C_4)$alkylamino, di-$[(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo$(C_1-C_4)$alkoxy-$(C_1-C_4)$alkyl, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di-$[(C_1-C_4)$alkyl]amino-$(C_1-C_4)$alkyl, $(C_3-C_9)$cycloalkylamino-$(C_1-C_4)$alkyl, $(C_3-C_9)$cycloalkyl, $(C_3-C_9)$heterocyclyl-$(C_1-C_4)$alkyl having 3 to 9 ring members, the cyclic groups in the last mentioned 3 radicals being unsubstituted or substituted by one or more radicals, preferably up to three radicals, from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, aminocarbonyl, $(C_1-C_4)$alkylaminocarbonyl, phenoxy-$(C_1-C_4)$alkyl, phenyl-$(C_1-C_4)$alkyl, heterocyclyl, heterocyclylamino, heterocyclyloxy, heterocyclylthio, or one of the last mentioned 16 radicals which is substituted in the acyclic moiety or, preferably, in the cyclic moiety by one or more radicals from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl, $(C_1-C_4)$alkoxy, heterocyclyl in the radicals in each case containing 3 to 9 ring atoms and 1 to 3 hetero ring atoms from the group consisting of N, O and S, $R^5$ is hydrogen, $(C_1-C_4)$alkyl, $(C_1-C_4)$haloalkyl or $(C_3-C_6)$cycloalkyl, A is a divalent radical of said formula $A^1$, $A^2$, $A^3$ or $A^4$, $R^6, R^7, R^8, R^9, R^{10}, R^{11}, R^{12}, R^{13}, R^{14}, R^{15}, R^{16}, R^{17}, R^{18}$ and $R^{19}$ each independently of one another are hydrogen, halogen, $(C_1-C_8)$alkyl, $(C_2-C_6)$alkenyl, $(C_2-C_6)$alkynyl, $(C_3-C_9)$cycloalkyl, $(C_3-C_9)$cycloalkenyl, phenyl, heterocyclyl having 3 to 6 ring atoms and 1 to 3 hetero ring atoms from the group consisting of N, O and S, each of the last mentioned 7 radicals being unsubstituted or substituted by one or more radicals from the group consisting of halogen, $(C_1-C_4)$alkoxy, $(C_1-C_4)$haloalkoxy, $(C_1-C_4)$alkylthio, amino, mono- and di$[(C_1-C_4)$alkyl]amino, $(C_1-C_4)$alkanoylamino, benzoylamino, nitro, cyano, $[(C_1-C_4)$alkyl]carbonyl, formyl, carbamoyl, mono- and di-$[(C_1-C_4)$alkyl]aminocarbonyl, $(C_1-C_4)$alkylsulfonyl and, in the case of cyclic radicals, also($C_1$–$C_4$)alkyl and ($C_1$–$C_4$)haloalkyl, ($X$)$_n$ is n substituents X and in this case X in each case independently of one another is halogen, hydroxyl, amino, nitro, formyl, carboxyl, cyano, thiocyanato, ($C_1$–$C_4$)alkyl, cyano-($C_1$–$C_4$)alkyl, ($C_1$–$C_4$)alkoxy, ($C_1$–$C_4$)alkylamino, di-[($C_1$–$C_4$)alkyl]amino, halo-($C_1$–$C_4$)alkyl, hydroxy-($C_1$–$C_4$)alkyl, ($C_1$–$C_4$)alkoxy-($C_1$–$C_4$)alkyl, halo($C_1$–$C_4$)alkoxy-($C_1$–$C_4$)alkyl, ($C_1$–$C_4$)alkylthio, halo-($C_1$–$C_4$)alkylthio, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$)alkylamino-($C_1$–$C_4$)alkyl, di-[($C_1$–$C_4$)alkyl]-amino-($C_1$–$C_4$)alkyl, ($C_3$–$C_9$)cycloalkylamino-($C_1$–$C_4$)alkyl, ($C_3$–$C_9$)cycloalkyl, heterocyclyl-($C_1$–$C_4$)alkyl having 3 to 9 ring members, the cyclic groups in the last mentioned 3 radicals being unsubstituted or substituted by one or more radicals, preferably up to three radicals, from the group consisting of ($C_1$–$C_4$)alkyl, halogen and cyano or phenyl, phenoxy, phenylcarbonyl, phenylcarbonyl-($C_1$–$C_4$)alkyl, ($C_1$–$C_4$)alkoxycarbonyl-($C_1$–$C_4$)alkyl, ($C_1$–$C_4$)alkylaminocarbonyl-($C_1$–$C_4$)alkyl, ($C_1$–$C_4$)alkylcarbonyl, ($C_1$–$C_4$)alkoxycarbonyl, aminocarbonyl, ($C_1$–$C_4$)alkylaminocarbonyl, phenoxy-($C_1$–$C_4$)alkyl, phenyl-($C_1$–$C_4$)alkyl, heterocyclyl, heterocyclylamino, heterocyclyloxy, heterocyclylthio or one of the last mentioned 16 radicals, which is substituted in the acyclic moiety or, preferably, in the cyclic moiety by one or more radicals from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$)haloalkoxy, formyl, ($C_1$–$C_4$)alkylcarbonyl, ($C_1$–$C_4$)alkoxycarbonyl, ($C_1$–$C_4$)alkoxy, heterocyclyl in the radicals in each case containing 3 to 9 ring atoms and 1 to 3 hetero ring atoms from the group consisting of N, O and S, or two adjacent radicals X together are a fused cyclic system having 4 to 6 ring atoms, which is carbocyclic or contains hetero ring atoms from the group consisting of O, S and N and which is unsubstituted or substituted by one or more radicals from the group consisting of halogen, ($C_1$–$C_4$)alkyl and oxo.

Of particular interest are furthermore compounds of the formula (I) according to the invention and their salts, in which $R^1$ is ($C_1$–$C_4$)alkyl, ($C_1$–$C_4$)haloalkyl, benzyl or [($C_3$–$C_6$)cycloalkyl]($C_1$–$C_2$)alkyl, $R^2$ and $R^3$ independently of one another are hydrogen, amino, formyl, ($C_1$–$C_4$)alkyl, ($C_1$–$C_4$)alkoxy-($C_1$–$C_4$)alkyl, ($C_2$–$C_6$)alkenyl, ($C_2$–$C_6$)alkynyl, ($C_1$–$C_4$)alkylamino-($C_1$–$C_4$)alkyl, di-[($C_1$–$C_4$)alkyl]amino-($C_1$–$C_4$)alkyl or phenyl, phenyl-($C_1$–$C_4$)alkyl or phenoxycarbonyl or one of the last mentioned three radicals, which is substituted in the phenyl moiety up to three times by radicals from the group consisting of halogen, ($C_1$–$C_4$)alkyl, ($C_1$–$C_4$)alkoxy and ($C_1$–$C_4$)alkoxycarbonyl, or $R^2$ and $R^3$ together with the nitrogen atom of the group $NR^2R^3$ are a heterocyclic radical having 3 to 6 ring atoms and 1 to 2 hetero ring atoms, in addition to the nitrogen atom the possible further hetero ring atom being selected from the group consisting of N and O and the radical being unsubstituted or substituted by one or more radicals from the group consisting of halogen, ($C_1$–$C_4$)alkyl and oxo, $R^4$ is hydrogen, amino, formyl, ($C_1$–$C_4$)alkyl, di-[($C_1$–$C_4$)alkyl]amino, ($C_1$–$C_4$)alkoxy-($C_1$–$C_4$)alkyl, ($C_2$–$C_6$)alkenyl, ($C_2$–$C_6$)alkynyl, ($C_1$–$C_4$)dialkylamino-($C_1$–$C_4$)alkyl, phenyl, phenoxy-($C_1$–$C_4$)alkyl, phenyl-($C_1$–$C_4$)alkyl, phenoxycarbonyl, phenylaminocarbonyl or one of the last mentioned five radicals, which is substituted in the phenyl moiety one to three times by radicals from the group consisting of halogen, ($C_1$–$C_4$)alkyl, ($C_1$–$C_4$)alkoxy and ($C_1$–$C_4$)alkoxycarbonyl, $R^5$ is hydrogen, ($C_1$–$C_4$)alkyl, ($C_1$–$C_4$)haloalkyl or ($C_3$–$C_6$)cycloalkyl, A is a divalent radical of said formula $A^1$, $A^2$, $A^3$ or $A^4$, $R^6, R^7, R^8, R^9, R^{10}, R^{11}, R^{12}, R^{13}, R^{14}, R^{15}, R^{16}, R^{17}, R^{18}$ and $R^{19}$ each independently of one another are hydrogen, halogen or ($C_1$–$C_4$)alkyl, preferably H or ($C_1$–$C_4$)alkyl, ($X$)$_n$ is n substituents X and in this case X in each case independently of one another is halogen, hydroxyl, ($C_1$–$C_4$)alkyl or ($C_1$–$C_4$)alkoxy.

Preferred compounds of the formula (I) according to the invention and their salts are those in which $R^1$ is ($C_1$–$C_4$)alkyl, ($C_1$–$C_4$)haloalkyl or [($C_3$–$C_6$)cycloalkyl]methyl, preferably —$CH_3$, —$CH_2F$, —$CHF_2$, —$CF_3$, —$CH_2Cl$, —$CHCl_2$, —$CCl_3$, —$CH_2Br$, —$CHBr_2$, —$CH_2CH_3$, —$CH_2CH_2F$, —$CF_2CHF_2$, —$CH_2CH_2Cl$, —$CH_2CH_2Br$, —$CH(CH_3)_2$, —$CF(CH_3)_2$, —$C(CH_3)_2Cl$, —$CH_2CH_2CH_2F$, —$CH_2CH_2CH_2Cl$ or cyclopropylmethyl, $R^2$ and $R^3$ independently of one another are hydrogen, amino, formyl or ($C_1$–$C_4$)alkyl or $R^2$ and $R^3$ together with the nitrogen atom of the group $NR^2R^3$ are a heterocyclic radical having 4 to 6 ring atoms and 1 to 2 hetero ring atoms, in addition to the nitrogen atom the possible further hetero ring atom being selected from the group consisting of N and O, $R^4$ is hydrogen or ($C_1$–$C_4$)alkyl, $R^5$ is H, ($C_1$–$C_4$)alkyl or ($C_1$–$C_4$)haloalkyl, preferably H, $CH_3$, $C_2H_5$, n- or i-$C_3H_7$, n-butyl, $CF_3$ or $CH_2CF_3$, in particular $CH_3$, A is a divalent radical of said formula $A^1$, $A^2$ or $A^3$, $R^6, R^7, R^8, R^9, R^{10}, R^{11}, R^{12}$ and $R^{13}$ each independently of one another are hydrogen or ($C_1$–$C_4$)alkyl, ($X$)$_n$ is n substituents X and in this case X in each case independently of one another is halogen, hydroxyl, ($C_1$–$C_4$)alkyl or ($C_1$–$C_4$)alkoxy.

Preferred compounds of the formula (I) according to the invention and their salts are also those which contain one or more of the features of the abovementioned preferred compounds.

The present invention also relates to processes for the preparation of the compounds of the formula (I) or their salts, which comprise a) reacting a compound of the formula (II)

$$R^1\text{—Fu} \quad (II)$$

in which Fu is a functional group from the group consisting of carboxylic acid ester, carboxylic acid orthoester, carboxylic acid chloride, carboxamide, carboxylic anhydride and trichloromethyl, with a biguanidide of the formula (III) or an acid addition salt thereof or

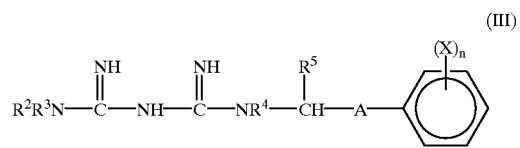

(III)

b) reacting a compound of the formula (IV)

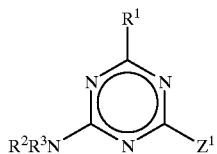

(IV)

in which $Z^1$ is a replaceable radical or a leaving group, e.g. chlorine, trichloromethyl, $(C_1-C_4)$alkylsulfonyl and unsubstituted or substituted phenyl-$(C_1-C_4)$ alkylsulfonyl or $(C_1-C_4)$alkylphenylsulfonyl, with a suitable amine of the formula (V) or an acid addition salt thereof

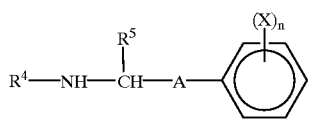

(V)

where in the formulae (II), (III), (IV) and (V) the radicals $R^1$, $R^2$, $R^3$, $R^4$, $R^5$, A and X and also n are as defined in formula (I).

The reaction of the compounds of the formulae (II) and (III) is preferably carried out under base catalysis in an inert organic solvent, such as, for example, tetrahydrofuran (THF), dioxane, acetonitrile, dimethylformamide (DMF), methanol or ethanol, at temperatures between $-10°$ C. and the boiling point of the solvent, preferably at 20° C. to 60° C.; if acid addition salts of the formula (III) are used, these are generally liberated in situ with the aid of a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicyclo[5.4.0] undec-7-ene (DBU). The respective base is in this case employed, for example, in the range from 0.1 to 3 mol equivalents, relative to the compound of the formula (III). In relation to the compound of the formula (III), the compound of the formula (II) can be employed, for example, in equimolar amounts or with an excess of up to 2 mol equivalents. Fundamentally, the appropriate processes are known in the literature (compare: Comprehensive Heterocyclic Chemistry, A. R. Katritzky, C. W. Rees, Pergamon Press, Oxford, N.Y., 1984, Vol.3; Part 2B; ISBN 0-08-030703-5, p.290).

The reaction of the compounds of the formulae (IV) and (V) is preferably carried out under base catalysis in an inert organic solvent, such as, for example, THF, dioxane, acetonitrile, DMF, methanol or ethanol, at temperatures between $-10°$ C. and the boiling point of the respective solvent or solvent mixture, preferably at 20° C. to 60° C., the compound (V), if employed as an acid addition salt, optionally being liberated in situ using a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicyclo[5.4.0]undec-7-ene (DBU). The respective base is in this case generally employed in the range from 1 to 3 mol equivalents relative to the compound of the formula (IV), the compound of the formula (IV) can be employed, for example, in an equimolar amount relative to the compound of the formula (V) or with an excess of up to 2 mol equivalents. Fundamentally, the appropriate processes are known from the literature (cf. Comprehensive Heterocyclic Chemistry, A. R. Katritzky, C. W. Rees, Pergamon Press, Oxford, N.Y., 1984, Vol.3; Part 2B; ISBN 0-08-030703-5, P. 482).

The starting materials of the formulae (II), (III), (IV) and (V) are either commercially available or can be prepared by or analogously to processes known from the literature. The compounds can also be prepared, for example, by one of the processes described below.

The compound of the formula (IV), or a direct precursor thereof, can be prepared, for example, as follows:

1. By reaction of a compound of the formula (II) with an amidinothiourea derivative of the formula (VI)

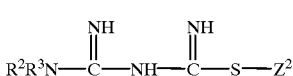

(VI)

in which $Z^2$ is $(C_1-C_4)$-alkyl or phenyl-$(C_1-C_4)$-alkyl and $R^2$ and $R^3$ are as defined in formula (I), compounds of the formula (IV) are obtained in which $Z^1$=—$SZ^2$.

2. By reaction of an amidine of the formula (VII) or of an acid addition salt thereof

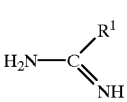

(VII)

in which $R^1$ is as defined in formula (I), with an N-cyanodithioiminocarbonate of the formula (VIII),

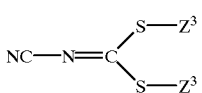

(VIII)

in which $Z^3$ is $(C_1-C_4)$-alkyl or phenyl-$(C_1-C_4)$-alkyl, compounds of the formula (IV) are obtained in which $Z^1$=—S—$Z^3$.

3. By reaction of an alkali metal dicyanamide with a carboxylic acid derivative of said formula (II), compounds of the formula (IV) are obtained in which $Z^1$=$NH_2$.

4. By reaction of trichloroacetonitrile with a nitrile of the formula (IX)

(IX)

in which $R^1$ is as defined in formula (I), firstly compounds of the formula (X)

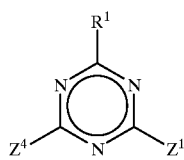

(X)

in which $Z^1$ and $Z^4$ are each $CCl_3$, are obtained, which by subsequent reaction with compounds of the formula $HNR^2R^3$ ($R^2$ and $R^3$ as in formula (I)) lead to compounds of the formula (IV) in which $Z^1=CCl_3$.

The reaction of the carboxylic acid derivatives of the formula (II) with the amidinothiourea derivatives of the formula (VI) is preferably carried out under base catalysis in an organic solvent, such as, for example, acetone, THF, dioxane, acetonitrile, DMF, methanol or ethanol, at temperatures from −10° C. to the boiling point of the solvent, preferably at 0° C. to 20° C. The reaction, however, can also be carried out in water or in aqueous solvent mixtures using one or more of the abovementioned organic solvents. If (VI) is employed as an acid addition salt, it can optionally be liberated in situ using a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicyclo[5.4.0]undec-7-ene (DBU). The respective base is in this case employed, for example, in the range from 1 to 3 mol equivalents relative to the compound of the formula (VI). Compounds of the formulae (II) and (VI) can be employed, for example, in an equimolar amount or in an excess of up to 2 mol equivalents of compound of the formula (II). Fundamentally, the appropriate processes are known from the literature (cf.: H. Eilingsfeld, H. Scheuermann, Chem. Ber.; 1967, 100, 1874); the corresponding intermediates of the formula (IV) are novel.

The reaction of the amidines of the formula (VII) with the N-cyanodithioiminocarbonates of the formula (VIII) is preferably carried out under base catalysis in an inert organic solvent, such as, for example, acetonitrile, DMF, dimethylacetamide (DMA), N-methylpyrrolidone (NMP), methanol or ethanol, at temperatures from −10° C. up to the boiling point of the solvent, preferably at 20° C. to 80° C. If (VII) is employed as an acid addition salt, it can optionally be liberated in situ using a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicyclo[5.4.0]undec-7-ene (DBU). The respective base is in this case employed, for example, in the range from 1 to 3 mol equivalents relative to the compound of the formula (VIII); compounds of the formula (VII) and (VIII) can generally be employed in an equimolar amount or in an excess of 2 mol equivalents of compound of the formula (II). Fundamentally, the corresponding processes are known from the literature (cf.: T. A. Riley, W. J. Henney, N. K. Dalley, B. E. Wilson, R. K. Robins; J. Heterocyclic Chem.; 1986, 23 (6), 1706–1714); the corresponding intermediates of the formula (IV) are novel.

The preparation of intermediates of the formula (X) where $Z^1$=chlorine can be carried out by reaction of alkali metal dicyanamide with a carboxylic acid derivative of the formula (II), Fu then preferably being the functional group carboxylic acid chloride or carboxamide. The reaction of the reaction components is carried out, for example, under acid catalysis in an inert organic solvent such as, for example, toluene, chlorobenzene or chlorinated hydrocarbons at temperatures between −10° C. and the boiling point of the solvent, preferably at 20° C. to 80° C., it being possible to chlorinate the resulting intermediates in situ using a suitable chlorinating reagent such as, for example, phosphorus oxychloride. Suitable acids are, for example, hydrohalic acids, such as HCl, or alternatively Lewis acids, such as, for example, $AlCl_3$ or $BF_3$ (cf. U.S. Pat. No. 5,095,113, DuPont).

The preparation of intermediates of the formula (X) where $Z^1$, $Z^4$=trihalomethyl can be carried out by reaction of the corresponding trihaloacetonitriles with a carbonitrile of the formula (IX). The reaction of the reaction components is carried out, for example, under acid catalysis in an inert organic solvent such as, for example, toluene, chlorobenzene or chlorinated hydrocarbons at temperatures between −40° C. and the boiling point of the solvent, preferably at −10° C. to 30° C. Suitable acids are, for example, hydrohalic acids such as HCl or alternatively Lewis acids such as, for example, $AlCl_3$ or $BF_3$ (cf. EP-A-130939, Ciba Geigy).

Intermediates of the formula (IV) in which $Z^1=(C_1-C_4)$ alkylmercapto or unsubstituted phenyl-$(C_1-C_4)$-alkylmercapto can be converted in an inert organic solvent such as, for example, toluene, chlorobenzene, chlorinated hydrocarbons or others at temperatures between −40° C. and the boiling point of the solvent, preferably at 20° C. to 80° C., using a suitable chlorinating reagent such as, for example, elemental chlorine or phosphorus oxychloride, to more reactive chlorotriazines of the formula (IV), in which $Z^1$=Cl (cf. J. K. Chakrabarti, D. E. Tupper; Tetrahedron 1975, 31(16), 1879–1882).

Intermediates of the formula (IV), where $Z^1=(C_1-C_4)$ alkylmercapto or unsubstituted phenyl-$(C_1-C_4)$-alkylmercapto or $(C_1-C_4)$alkylphenylthio, can be oxidized in a suitable solvent such as, for example, chlorinated hydrocarbons, acetic acid, water, alcohols, acetone or mixtures thereof at temperatures between 0° C. and the boiling point of the solvent, preferably from 20° C. to 80° C., using a suitable oxidizing reagent such as, for example, m-chloroperbenzoic acid, hydrogen peroxide or potassium peroxomonosulfate (cf.: T. A. Riley, W. J. Henney, N. K. Dalley, B. E. Wilson, R. K. Robins; J. Heterocyclic Chem.; 1986, 23 (6), 1706–1714).

The following acids are suitable for the preparation of the acid addition salts of the compounds of the formula (I): hydrohalic acids such as hydrochloric acid or hydrobromic acid, furthermore phosphoric acid, nitric acid, sulfuric acid, mono- or bifunctional carboxylic acids and hydroxycarboxylic acids such as acetic acid, maleic acid, succinic acid, fumaric acid, tartaric acid, citric acid, salicylic acid, sorbic acid or lactic acid, and also sulfonic acids such as p-toluenesulfonic acid or 1,5-naphthalenedisulfonic acid. The acid addition compounds of the formula (I) can be obtained in a simple manner by the customary salt formation methods, e.g. by dissolving a compound of the formula (I) in a suitable organic solvent such as, for example, methanol, acetone, methylene chloride or benzine and adding the acid at temperatures from 0 to 100° C., and are isolated in a known manner, for example by filtering off, and optionally purified by washing with an inert organic solvent.

The base addition salts of the compounds of the formula (I) are preferably prepared in inert polar solvents such as, for example, water, methanol, or acetone, at temperatures from 0 to 100° C. Suitable bases for the preparation of the salts according to the invention are, for example, alkali metal carbonates, such as potassium carbonate, alkali metal and alkaline earth metal hydroxides, e.g. NaOH or KOH, alkali metal and alkaline earth metal hydrides, e.g. NaH, alkali metal and alkaline earth metal alkoxides, e.g. sodium methoxide, potassium tert-butoxide, or ammonia or ethanolamine.

By the "inert solvents" designated in the above process variants, solvents are in each case intended which are inert under the particular reaction conditions, but do not have to be inert under all reaction conditions.

The compounds of the formula (I) according to the invention and their salts, together designated as compounds of the formula (I) (according to the invention) in the following have an excellent herbicidal activity against a wide spectrum of economically important mono- and dicotyledonous harmful plants. Even perennial weeds which are difficult to control and which sprout from rhizomes, root stocks or other permanent organs, are well controlled by the active compounds. In this case it is immaterial whether the substances are applied prior to sowing, pre-emergence or post-emergence.

In detail, by way of example some representatives of the mono- and dicotyledonous weed flora may be mentioned which can be controlled by the compounds according to the invention without a restriction to certain species taking place as a result of naming them. On the side of monocotyledonous weed species, for example, Avena, Lolium, Alopecurus, Phalaris, Echinochloa, Digitaria, Setaria and also Cyperus species from the annual group and on the side of the perennial species Agropyron, Cynodon, Imperata as well as Sorghum and also perennial Cyperus species are well controlled. In the case of dicotyledonous weed species, the spectrum of action extends to species such as, for example, Galium, Viola, Veronica, Lamium, Stellaria, Amaranthus, Sinapis, Ipomoea, Matricaria, Abutilon and Sida on the annual side and Convolvulus, Cirsium, Rumex and Artemisia in the case of the perennial weeds.

Weeds occurring in rice under the specific cultivation conditions, such as, for example, Sagittaria, Alisma, Eleocharis, Scirpus and Cyperus are likewise excellently controlled by the active compounds according to the invention.

If the compounds according to the invention are applied to the surface of the earth before germination, either the emergence of the weed seedlings is completely prevented or the weeds grow to the seed leaf stage, but then cease their growth and then finally die off completely after three to four weeks have passed.

When the active compounds are applied to the green parts of plants post-emergence, a drastic stop in growth likewise occurs very rapidly after the treatment and the weed plants stay in the growth stage present at the time of application or die off completely after a certain time, so that in this way weed competition harmful for the crop plants is eliminated very early and in a lasting manner.

Although the compounds according to the invention have an excellent herbicidal activity against mono- and dicotyledonous weeds, crop plants of economically important crops such as, for example, wheat, barley, rye, rice, corn, sugar beet, cotton and soybeans are only damaged insignificantly or not at all. For these reasons, the present compounds are very highly suitable for the selective control of undesired vegetation in agricultural crop plantations.

Moreover, the substances according to the invention have outstanding growth-regulatory properties in crop plants. They intervene in a regulating manner in the plants' own metabolism and can thus be employed for affecting plant constituents in a controlled manner and for facilitating harvesting, such as, for example, by causing desiccation and stunting of growth. In addition, they are also suitable for the general control and inhibition of undesired vegetative growth without at the same time destroying the plants. In many monocotyledonous and dicotyledonous crops, inhibition of vegetative growth plays a large part, as lodging can be decreased or completely prevented by this means.

The compounds according to the invention can be used in the customary preparations in the form of wettable powders, emulsifiable concentrates, sprayable solutions, dusting compositions or granules. The invention therefore also relates to herbicidal and plant growth-regulating compositions which contain compounds of the formula (I).

Compounds of the formula (I) can be formulated in various ways, depending on which biological and/or physicochemical parameters are specified. Suitable formulation possibilities are, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions on an oil or water basis, oil-miscible solutions, capsule suspensions (CS), dusting compositions (DP), dressing agents, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie", [Chemical Technology], Volume 7, C. Hauser Verlag Munich, 4th edition 1986, Wade van Valkenburg, "Pesticide Formulations", Marcel Dekker, New York, 1973; K. Martens, "Spray Drying" Handbook, 3rd Ed. 1979, G. Goodwin Ltd. London.

The necessary formulation aids such as inert materials, surfactants, solvents and other additives are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, New York; C. Marsden, "Solvents Guide"; 2nd Ed., Interscience, New York 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., New York 1964; Shöfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

On the basis of these formulations, combinations with other pesticidally active substances, such as, for example, insecticides, acaricides, herbicides and fungicides, and also with safeners, fertilizers and/or growth regulators, can also be prepared, e.g. in the form of a finished formulation or as a tank mix.

Wettable powders are preparations which are uniformly dispersible in water and which, in addition to the active compound, apart from a diluent or inert substance also contain surfactants of ionic and/or nonionic type (wetting agents, dispersants), e.g. polyethoxylated alkyl phenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'- disulfonate, sodium dibutylnaphthalenesulfonate or alternatively sodium oleoylmethyltaurate. To prepare the wettable powders, the herbicidal active compounds are finely ground, for example in customary equipment such as hammer mills, blowing mills and air-jet mills, and simultaneously or subsequently mixed with the formulation aids.

Emulsifiable concentrates are prepared by dissolving the active compound in an organic solvent, e.g. butanol, cyclohexanone, dimethylformamide, xylene or alternatively relatively high-boiling aromatics or hydrocarbons or mixtures of the organic solvents with addition of one or more surfactants of ionic and/or nonionic type (emulsifiers). Emulsifiers which can be used, for example, are: calcium alkylarylsulfonates such as Ca dodecylbenzenesulfonate or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters such as, for example, sorbitan fatty acid esters or polyoxyethylene sorbitan esters such as, for example, polyoxyethylene sorbitan fatty acid esters.

Dusting compositions are obtained by grinding the active compound with finely divided solid substances, e.g. talc, natural clays, such as kaolin, bentonite and pyrophyllite, or diatomaceous earth.

Suspension concentrates can be on a water or oil basis. They can be prepared, for example, by wet grinding by means of commercially available bead mills and, if appropriate, addition of surfactants, such as, for example, have already been mentioned above in the case of the other types of formulation.

Emulsions, e.g. oil-in-water emulsions (EW), can be prepared, for example, by means of stirrers, colloid mills and/or static mixers using aqueous organic solvents and, if appropriate, surfactants, such as, for example, have already been mentioned above in the case of the other types of formulation.

Granules can either be prepared by jet application of the active compound to adsorptive, granulated inert material or by applying active compound concentrates by means of adhesives, e.g. polyvinyl alcohol, sodium polyacrylate or alternatively mineral oils, to the surface of carriers such as sand, kaolinites or of granulated inert material. Suitable active compounds can also be granulated in the manner customary for the preparation of fertilizer granules—if desired as a mixture with fertilizers.

Water-dispersible granules are generally prepared by the customary processes such as spray drying, fluidized bed granulation, disc granulation, mixing using high-speed mixers and extrusion without solid inert material. To prepare disk, fluidized bed, extruder and spray granules see, for example, processes in the "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8–57.

For further details on the formulation of plant protection agents, see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

The agrochemical preparations generally contain 0.1 to 99% by weight, in particular 0.1 to 95% by weight, of active compound of the formula (I). In wettable powders the active compound concentration is, for example, approximately 10 to 90% by weight, the remainder to 100% by weight consists of customary formulation constituents. In the case of emulsifiable concentrates the active compound concentration can be approximately 1 to 90, preferably 5 to 80, % by weight. Formulations in the form of dust contain 1 to 30% by weight of active compound, preferably at most 5 to 20% by weight of active compound, sprayable solutions contain approximately 0.05 to 80, preferably 2 to 50% by weight of active compound. In the case of water-dispersible granules the active compound content partly depends on whether the active compound is present in liquid or solid form and which granulating aids, fillers, etc. are used. In the case of the water-dispersible granules, the content of active compound lies, for example, between 1 and 95% by weight, preferably between 10 and 80% by weight.

In addition, said active compound formulations if appropriate contain the adhesives, wetting agents, dispersants, emulsifiers, penetrating agents, preservatives, frost protection agents and solvents, fillers, carriers and colorants, antifoams, evaporation inhibitors and agents affecting the pH and the viscosity which are customary in each case.

Combination components which can be employed for the active compounds according to the invention in mixture formulations or in the tank mix are, for example, known active compounds, such as are described in, for example, Weed Research 26, 441–445 (1986), or "The Pesticide Manual", 10th edition, The British Crop Protection Council and the Royal Soc. of Chemistry, 1994 and references cited there. Herbicides known from the literature, which can be combined with the compounds of the formula (I), which can be mentioned are, for example, the following active compounds (note: the compounds are either designated by the "common name" according to the International Organization for Standardization (ISO) or by the chemical names, if appropriate together with a customary code number): acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and methyl ester; alachlor; alloxydim; ametryn; amidosulfuron; amitrole; AMS, i.e. ammonium sulfamate; anilofos; asulam; atrazine; azimsulfurone (DPX-A8947); aziprotryne; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyldithiocarbamate, chlomethoxyfen; chloramben; chlorazifop-butyl, chlormesulon (ICI-A0051); chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (e.g. clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (e.g. butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazone; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (e.g. ethyl ester, HN-252); etobenzanid (HW 52); fenoprop; fenoxan, fenoxaprop and fenoxaprop-P and also their esters e.g. fenoxaprop-P-ethyl and fenoxaprop-ethyl; fenoxydim; fenuron; flamprop-methyl; flazasulfuron; fluazifop and fluazifop-P and their esters, e.g. fluazifop-butyl and fluazifop-P-butyl; fluchloralin; flumetsulam; flumeturon; flumiclorac and its esters (e.g. pentyl ester, S-23031); flumioxazin (S482); flumipropyn; flupoxam (KNW-739); fluorodifen; fluoroglycofen-ethyl; flupropacil (UBIC-4243); fluridone; fluorochloridone; fluroxypyr; flurtamone; fomesafen; fosamine; furyloxyfen; glufosinate; glyphosate; halosafen; halosulfuron and its esters (e.g. methyl ester, NC-319); haloxyfop and its esters, haloxyfop-P (=R-haloxyfop) and its esters; hexazinone; imazamethabenzmethyl; imazapyr; imazaquin and salts such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidide; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (e.g. propargyl ester); quinclorac; quinmerac; quinofop and its ester derivatives, quizalofop und quizalofop-P and their ester derivatives e.g. quizalofop-ethyl; quizalofop-P-tefuryl und -ethyl; renriduron; rimsulfuron (DPX-E 9636); S 275, i.e. 2-[4-chloro-2-fluoro-5-(2-propynyloxy)phenyl]4,5,6,7-tetrahydro-2H-indazole; secbumeton; sethoxydim; siduron; simazine; simetryn; SN 106279, i.e. 2-[[7-[2-chlor-4-(trifluoro-methyl)phenoxy]-2-naphthalenyl]oxy]propanoic acid and methyl esters; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thizopyr (Mon-13200); thidiazimin (SN-24085); thifensulfuron-methyl; thiobencarb; tiocarbazil; tralkoxydim; tri-allate; triasulfuron; triazofenamide; tribenuron-methyl; triclopyr; tridiphane; trietazine; trifluralin; triflusulfuron and esters (e.g. methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations present in commercially available form are optionally diluted in the customary manner, e.g. in the case of wettable powders, emulsifiable concentrates, dispersions and water-dispersible granules by means of water. Preparations in the form of dust, soil or broadcasting granules and sprayable solutions are customarily not diluted further with other inert substances before use.

The required application rate of the compounds of the formula (I) varies with the external conditions such as temperature, humidity, the nature of the herbicide used, inter alia. It can vary within wide limits, e.g. between 0.001 and 10.0 kg/ha or more active substance, but it is preferably between 0.005 and 5 kg/ha.

A. CHEMICAL EXAMPLES

Example A1

2-Amino-4-(1,1,2,2-tetrafluoroethyl)-6-(1-phenyl-3-butylamino)-1,3,5-triazine (see Table 1, Example 55)

A methoxide solution prepared from 1.2 g (0.05 mol) of sodium and 100 ml of methanol is added to 6.7 g (0.025 mol) of 3-biguanidino-1-phenylbutane hydrochloride in 50 ml of methanol and 7 g of ground molecular sieve 3. 7.2 g (0.045 mol) of methyl 1,1,2,2-tetrafluoropropanoate are then added and the mixture is stirred for 2 hours at 25° C. and then for 4 hours at 65° C. The reaction mixture is filtered, the filtrate is concentrated and the residue is taken up in ethyl acetate. It is washed with water and dried using sodium sulfate. The drying agent is filtered off and the solvent is evaporated in vacuo. After purification by column chromatography (eluent: ethyl acetate), 6.95 g (81% of theory) of 2-amino-4-(1,1,2,2-tetrafluoroethyl)-6-(1-phenyl-3-butylamino)-1,3,5-triazine are obtained.

Example A2

2-Amino-4-isopropyl-6-[1-(4-fluorophenyl)-3-butylamino]-1,3,5-triazine (see Table 1, Example 2)

2.6 g (0.015 mol) of 2-amino-4-chloro-6-isopropyl-1,3,5-triazine and 2.1 g (0.015 mol) of $K_2CO_3$ are initially introduced in 50 ml of acetonitrile. 2.5 g (0.015 mol) of 1-(4-fluorophenyl)-3-butylamine, dissolved in 20 ml of acetonitrile, are added dropwise to this solution. It is then heated to reflux for 3 hours. The solid constituents are then filtered off with suction and the filtrate is concentrated in a rotary evaporator. The residue is purified by means of column chromatography (eluent: ethyl acetate). Yield: 4.1 g (90% of theory).

The compounds described in the following Tables 1 and 2 are obtained according to or analogously to the above Examples A1 and A2. In the tables:

| No. | | Example or Example number |
|---|---|---|
| Phys. Data | = | Characteristic physical data of the compound |
| Me | = | Methyl |
| Et | = | Ethyl |
| Pr | = | Propyl |
| i-Pr | = | Isopropyl |
| c-Pr | = | Cyclopropyl |
| t-Bu | = | tertiary butyl |
| Ph | = | Phenyl |
| $(X)_n$ | = | Position and nature of the substituents on the phenyl ring (Position 1 = bond to A); |
| "—" | = | no substituent on the phenyl ring (n = 0) |

TABLE 1

Compounds of the formula (I))

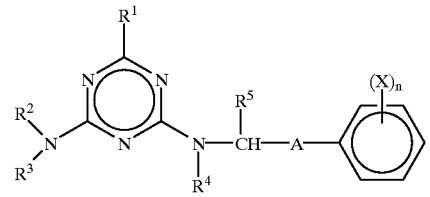

(I)

| No. | $R^1$ | $R^2$ | $R^3$ | $R^4$ | $R^5$ | A | $(X)_n$ | Phys. Data |
|---|---|---|---|---|---|---|---|---|
| 1 | i-Pr | H | H | H | Me | $(CH_2)_2$ | — | NMR, see end of table |
| 2 | i-Pr | H | H | H | Me | $(CH_2)_2$ | 4-F | NMR, see end of table |
| 3 | i-Pr | H | H | H | Me | $(CH_2)_2$ | 2-Cl | NMR, see end of table |
| 4 | i-Pr | H | H | H | Me | $(CH_2)_2$ | 3,5-$Me_2$ | NMR, see end of table |
| 5 | i-Pr | H | H | H | Me | $(CH_2)_2$ | 4-(t-Bu) | Oil |
| 6 | i-Pr | H | H | H | Me | $(CH_2)_2$ | 3-I | Oil |
| 7 | i-Pr | H | H | H | Me | $(CH_2)_2$ | 2,5-$Me_2$ | |
| 8 | i-Pr | H | H | H | Me | $(CH_2)_2$ | 2,6-$Cl_2$ | |
| 9 | i-Pr | H | H | H | Me | $(CH_2)_2$ | 2,4,6-$Me_3$ | Oil |
| 10 | i-Pr | H | H | H | Me | $(CH_2)_2$ | 3,5-$F_2$ | |
| 11 | i-Pr | H | H | H | Me | $(CH_2)_2$ | 3-Me | Oil |
| 12 | i-Pr | H | H | H | Me | $(CH_2)_2$ | 3-$CF_3$ | |
| 13 | i-Pr | H | H | H | Me | $(CH_2)_2$ | 3-Br | |
| 14 | i-Pr | H | H | H | Me | $(CH_2)_2$ | 4-Me | |
| 15 | t-Bu | H | H | H | Me | $(CH_2)_2$ | 3,5-$Me_2$ | |
| 16 | Me | H | H | H | Me | $(CH_2)_2$ | 3,4,5-$Me_3$ | |
| 17 | Et | H | H | H | Me | $(CH_2)_2$ | 3,5-$Me_2$ | |
| 18 | $CH_2CH_2F$ | H | H | H | Me | $(CH_2)_2$ | 2,4,6-$Me_3$ | |
| 19 | $CH_2CH_2Cl$ | H | H | H | Me | $(CH_2)_2$ | 2-Me | |
| 20 | $CH_2CH_2Br$ | H | H | H | Me | $(CH_2)_2$ | 2-Cl | |
| 21 | $C(CH_3)_2Cl$ | H | H | H | Me | $(CH_2)_2$ | 2-Br | |
| 22 | $CH_2CH_2CH_2F$ | H | H | H | Me | $(CH_2)_2$ | 2-I | |
| 23 | $CH_2CH_2CH_2Cl$ | H | H | H | Me | $(CH_2)_2$ | 2-$CCl_3$ | |
| 24 | $CF_3$ | H | H | H | Me | $(CH_2)_2$ | — | |
| 25 | $CF_3$ | H | H | H | Me | $(CH_2)_2$ | 3,5-$F_2$ | |
| 26 | $CF_3$ | H | H | H | Me | $(CH_2)_2$ | 3,5-$Cl_2$ | |
| 27 | $CF_3$ | H | H | H | Me | $(CH_2)_2$ | 3,5-$Me_2$ | |
| 28 | $CF_3$ | H | H | H | Me | $(CH_2)_2$ | 3,5-$Br_2$ | |
| 29 | $CH_2F$ | H | H | H | Me | $(CH_2)_2$ | 4-Me | |
| 30 | $CHF_2$ | H | H | H | Me | $(CH_2)_2$ | 4-Cl | |
| 31 | $CH_2Cl$ | H | H | H | Me | $(CH_2)_2$ | 3,5-$Me_2$ | |
| 32 | $CHCl_2$ | H | H | H | Me | $(CH_2)_2$ | 3-Me | |
| 33 | $CCl_3$ | H | H | H | Me | $(CH_2)_2$ | 3-Cl | |
| 34 | $CH_2Br$ | H | H | H | Me | $(CH_2)_2$ | 3-I | |
| 35 | $CHBr_2$ | H | H | H | Me | $(CH_2)_2$ | 3-I | |
| 36 | $CF(CH_3)_2$ | H | H | H | Me | $(CH_2)_2$ | 4-(i-Pr) | |
| 37 | $CF(CH_3)_2$ | H | H | H | Me | $(CH_2)_2$ | — | NMR, see end of table |
| 38 | $CF(CH_3)_2$ | H | H | H | Me | $(CH_2)_2$ | 4-F | NMR, see end of table |
| 39 | $CF(CH_3)_2$ | H | H | H | Me | $(CH_2)_2$ | 3,5-$Me_2$ | NMR, see end of table |
| 40 | $CF(CH_3)_2$ | H | H | H | Me | $(CH_2)_2$ | 4-Me | NMR, see end |

TABLE 1-continued

Compounds of the formula (I))

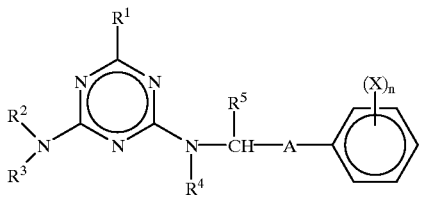

(I)

| No. | R¹ | R² | R³ | R⁴ | R⁵ | A | (X)ₙ | Phys. Data |
|---|---|---|---|---|---|---|---|---|
| | | | | | | | | of table |
| 41 | CF(CH₃)₂ | H | H | H | Me | (CH₂)₂ | 2-Cl | Oil |
| 42 | CF(CH₃)₂ | H | H | H | Me | (CH₂)₂ | 4-(t-Bu) | |
| 43 | CF(CH₃)₂ | H | H | H | Me | (CH₂)₂ | 3-I | Oil |
| 44 | CF(CH₃)₂ | H | H | H | Me | (CH₂)₂ | 2,5-Me₂ | |
| 45 | CF(CH₃)₂ | H | H | H | Me | (CH₂)₂ | 2,6-Cl₂ | |
| 46 | CF(CH₃)₂ | H | H | H | Me | (CH₂)₂ | 2,4,6-Me₃ | Oil |
| 47 | CF(CH₃)₂ | H | H | H | Me | (CH₂)₂ | 3,5-F₂ | |
| 48 | CF(CH₃)₂ | H | H | H | Me | (CH₂)₂ | 3-Me | Oil |
| 49 | CF(CH₃)₂ | H | H | H | Me | (CH₂)₂ | 3-CF₃ | Oil |
| 50 | CF(CH₃)₂ | H | H | H | Me | (CH₂)₂ | 3-Br | |
| 51 | CF(CH₃)₂ | H | H | H | Me | (CH₂)₂ | 3,5-Me₂, 4-I | |
| 52 | CF(CH₃)₂ | H | H | H | Me | (CH₂)₂ | 3-OMe | |
| 53 | CF(CH₃)₂ | H | H | H | Me | (CH₂)₂ | 3,5-(OMe)₂ | |
| 54 | CF(CH₃)₂ | H | H | H | Me | (CH₂)₂ | 4-OMe | |
| 55 | CF₂CHF₂ | H | H | H | Me | (CH₂)₂ | — | NMR, see end of table |
| 56 | CF₂CHF₂ | H | H | H | Me | (CH₂)₂ | 3,5-Me₂ | |
| 57 | CF₂CHF₂ | H | H | H | Me | (CH₂)₂ | 3,4,5-Me₃ | |
| 58 | CF₂CHF₂ | H | H | H | Me | (CH₂)₂ | 3,5-F₂ | |
| 59 | CF₂CHF₂ | H | H | H | Me | (CH₂)₂ | 2,5-Me₂ | |
| 60 | CF₂CHF₂ | H | H | H | Me | (CH₂)₂ | 3-Me | |
| 61 | CF₂CHF₂ | H | H | H | Me | (CH₂)₂ | 3-CF₃ | |
| 62 | CF₂CF₃ | H | H | H | Me | (CH₂)₂ | — | |
| 63 | CF₂CF₃ | H | H | H | Me | (CH₂)₂ | 3,5-Me₂ | |
| 64 | CF₂CF₃ | H | H | H | Me | (CH₂)₂ | 3,5-Me₂, 4-I | |
| 65 | CF₂CF₃ | H | H | H | Me | (CH₂)₂ | 4-OMe | |
| 66 | CF₂CF₃ | H | H | H | Me | (CH₂)₂ | 4-OEt | |
| 67 | i-Pr | NH₂ | H | H | Me | (CH₂)₂ | 4-NO₂ | |
| 68 | Me | NH₂ | H | H | Me | (CH₂)₂ | 4-CF₃ | |
| 69 | CF(CH₃)₂ | NH₂ | H | H | Me | (CH₂)₂ | 3-OCH₃ | |
| 70 | CF(CH₃)₂ | CHO | H | H | Me | (CH₂)₂ | 3-OC₂H₅ | |
| 71 | CF₂CHF₂ | CHO | H | H | Me | (CH₂)₂ | 2-CN | |
| 72 | CH₂CH₂Cl | CHO | H | H | Me | (CH₂)₂ | 4-I | |
| 73 | CF(CH₃)₂ | Me | H | H | Me | (CH₂)₂ | 3,5-Me₂ | |
| 74 | C(CH₃)₂Cl | Me | H | H | Me | (CH₂)₂ | — | |
| 75 | CF(CH₃)₂ | Et | H | H | Me | (CH₂)₂ | 3,5-F₂ | |
| 76 | Et | Pr | H | H | Me | (CH₂)₂ | 2,6-Cl₂ | |
| 77 | i-Pr | Me | Me | H | Me | (CH₂)₂ | 3-F | |
| 78 | i-Pr | Et | Et | H | Me | (CH₂)₂ | 3,5-Me₂ | |
| 79 | i-Pr | H | H | Me | Me | (CH₂)₂ | — | |
| 80 | CF(CH₃)₂ | H | H | Me | Me | (CH₂)₂ | 3,5-Me₂ | |
| 81 | CF₃ | H | H | Me | Et | (CH₂)₂ | 3-Me | |
| 82 | i-Pr | H | H | Et | H | (CH₂)₂ | 2,5-Me₂ | |
| 83 | CF(CH₃)₂ | H | H | Et | Me | (CH₂)₂ | 2,4-Cl₂ | |
| 84 | CF₂CHF₂ | H | H | Br | Me | (CH₂)₂ | 3,5-F₂ | |
| 85 | CF₂CF₂CF₃ | H | H | n-C₄H₉ | Me | (CH₂)₂ | 3-CF₃ | |
| 86 | CF(CH₃)₂ | H | H | H | H | (CH₂)₂ | — | Oil |
| 87 | i-Pr | H | H | H | H | (CH₂)₂ | — | Oil |
| 88 | CF(CH₃)₂ | H | H | H | H | (CH₂)₂ | 3,5-Me₂ | |
| 89 | i-Pr | H | H | H | H | (CH₂)₂ | 3,5-Me₂ | |
| 90 | CF(CH₃)₂ | H | H | H | Et | (CH₂)₂ | 3,5-Me₂ | |
| 91 | CF(CH₃)₂ | H | H | H | Et | (CH₂)₂ | — | Oil |
| 92 | CF(CH₃)₂ | H | H | H | n-Pr | (CH₂)₂ | 3,5-Me₂ | |
| 93 | CF(CH₃)₂ | H | H | H | n-Pr | (CH₂)₂ | — | |
| 94 | i-Pr | H | H | H | H | (CH₂)₃ | — | |
| 95 | i-Pr | H | H | H | H | (CH₂)₃ | 3,5-Me₂ | |
| 96 | Me | H | H | H | H | (CH₂)₃ | 3,4,5-Me₃ | |
| 97 | Et | H | H | H | H | (CH₂)₃ | 3,5-Me₂ | |
| 98 | Pr | H | H | H | H | (CH₂)₃ | 3,5-Me₂, 4-I | |
| 99 | CF(CH₃)₂ | H | H | H | H | (CH₂)₃ | — | Oil |
| 100 | CF(CH₃)₂ | H | H | H | H | (CH₂)₃ | 3,5-Me₂ | |
| 101 | CF(CH₃)₂ | H | H | H | H | (CH₂)₃ | 4-(t-Bu) | |
| 102 | CH₃ | H | H | H | Me | CHMeCH₂ | 3-OH | |

TABLE 1-continued

Compounds of the formula (I)

(I)

| No. | R¹ | R² | R³ | R⁴ | R⁵ | A | (X)$_n$ | Phys. Data |
|-----|-----|-----|-----|-----|-----|-----|-----|-----|
| 103 | C₄H₉ | H | H | H | Me | CHMeCH₂ | 4-OH | |
| 104 | t-Bu | H | H | H | Me | CH₂CHMe | 2-OH | |
| 105 | CF₂CF₂CF₃ | H | H | H | Me | CH₂CHMe | 3-OH | |
| 106 | CF(CH₃)₂ | H | H | H | Me | CH₂ | — | Oil |
| 107 | CF(CH₃)₂ | H | H | H | Me | CH₂ | 3,5-Me₂ | Oil |
| 108 | CF₂CHF₂ | H | H | H | Me | CH₂ | 4-F | |
| 109 | CF₂CF₂CF₃ | H | H | H | H | CH₂ | 4-F | |
| 110 | i-Pr | H | H | H | Me | —CH═CH— (E)-Form | — | Oil |
| 111 | i-Pr | H | H | H | Me | —CC— | — | |
| 112 | i-Pr | Me | H | H | Me | CHMeCH₂ | 3,5-Me₂ | Oil |
| 113 | i-Pr | Me | H | H | Et | (CH₂)₂ | — | Oil |
| 114 | i-Pr | Me | Me | H | Me | CHMeCH₂ | 3,5-Me | Oil |
| 115 | i-Pr | Me | Me | H | Et | (CH₂)₂ | — | Oil |
| 116 | i-Pr | Me | Me | H | Me | (CH₂)₂ | — | Oil |
| 117 | i-Pr | Me | H | H | Me | (CH₂)₂ | — | Oil |

NMR data for individual examples:

For Example 1: ¹H-NMR (DMSO-d₆): δ=1.10 (d, 3H); 1.15 (d, 6H); 1.68 (m, 1H); 1.80 (m, 1H); 2.61 (m, 1H); 4.01 (m, 1H); 7.2 (m, 5H).

For Example 2: ¹H-NMR (DMSO-d₆): δ=1.09 (d, 3H); 1.15 (d, 6H); 1.65 (m, 1H); 1.79 (m, 1H); 2.63 (m, 3H); 3.96 (m, 1H); 7.05 (m, 2H); 7.22 (m, 2H).

For Example 3: ¹H-NMR (DMSO-d₆): δ=1.13 (m, 9H); 1.74 (m, 2H); 8.55 (Septett, 1H); 2.70 (t, 2H); 4.00 (m, 1H); 7.3 (m, 4H).

For Example 4: ¹H-NMR (DCCl₃): δ=1.22 (d, 3H); 1.26 (d, 6H); 1.79 (m, 2H); 2.29 (s, 6H); 2.60 (m, 3H); 4.01 (m, 1H); 6.78 (s, 2H); 6.82 (s, 1H).

For Example 37: ¹H-NMR (CDCl₃): δ=1.1 (d, 3H); 1.6 (s, 3H); 1.7 (s, 3H); 2.7 (m, 3H); 7.1 (m, 3H); 7.2 (m, 3H).

For Example 38: ¹H-NMR (CDCl₃): δ=1.1 (d, 3H); 1.6 (s, 3H); 1.7 (s, 3H); 2.6 (m, 3H); 4.0 (m, 1H); 6.9 (m, 2H); 7.1 (m, 2H).

For Example 39: ¹H-NMR (CDCl₃): δ=1.2 (d, 3H); 1.6 (s, 3H); 1.7 (s, 3H); 1.8 (m, 2H); 2.6 (m, 2H); 4.1 (m, 1H); 6.8 (m, 2H); 6.9 (m, 1H).

For Example 40: ¹H-NMR (DMSO-d₆): δ=1.1 (d, 3H); 1.5 (s, 3H); 1.6 (s, 3H); 1.7 (m, 1H); 1.8 (m, 1H); 2.2 (s, 3H), 4.0 (m, 1H); 7.1 (s, 4H).

For Example 55: ¹H-NMR (DMSO-d₆): δ=1.1 (d, 3H); 1.7 (m, 2H); 2.6 (m, 3H); 4.0 (m, 1H); 6.7 (tt, 1H); 7.2 (m, 5H).

TABLE 2

Compounds of the formula (Ia)

(Ia)

| No. | R¹ | R⁵ | A | (X)$_n$ | Phys. Dat. |
|-----|-----|-----|-----|-----|-----|
| 2-1 | CH₂-c-Pr | Me | (CH₂)₂ | — | |
| 2-2 | CH₂-c-Pr | Et | (CH₂)₂ | — | |
| 2-3 | CH₂-c-Pr | Me | (CH₂)₂ | 3,-5-Me₂ | |
| 2-4 | CH₂-c-Pr | Et | (CH₂)₂ | 3,-5-Me₂ | |
| 2-5 | CH(CH₃)-c-Pr | Me | (CH₂)₂ | — | |

TABLE 2-continued

Compounds of the formula (Ia)

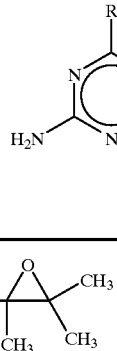

(Ia)

| No. | R¹ | R⁵ | A | (X)ₙ | Phys. Dat. |
|---|---|---|---|---|---|
| 2-6 | 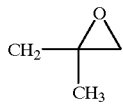 | Me | (CH₂)₂ | 3-Iodo | |
| 2-7 | 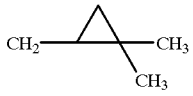 | Me | (CH₂)₂ | NMe₂ | |
| 2-8 | (cyclopropyl-C(CH₃)₂-CH₂-) | Me | (CH₂)₂ | 3,5-F₂ | |
| 2-9 | CH₂-3-CF₃—C₆H₃ | Et | (CH₂)₂ | 3-NMe₂ | |
| 2-10 | CH₂-3-F—C₆H₄ | Et | (CH₂)₂ | 3-NEt₂ | |
| 2-11 | CH₂-2,6-F₂—C₆H₃ | Me | (CH₂)₂ | 3-OPh | |
| 2-12 | CH₂-2,6-Cl₂—C₆H₃ | Me | (CH₂)₂ | 3-SPh | |
| 2-13 | Ph | Et | (CH₂)₂ | — | |
| 2-14 | 2-CH₃—C₆H₄ | Me | (CH₂)₂ | — | Oil |
| 2-15 | 2-F—C₆H₄ | Me | (CH₂)₂ | — | Oil |
| 2-16 | 3-OCH₃—C₆H₄ | Et | (CH₂)₂ | — | |
| 2-17 | 2,4-(CH₃)₂—C₆H₄ | i-Pr | (CH₂)₂ | — | |
| 2-18 | 3,5-(CH₃)₂—C₆H₃ | Me | (CH₂)₂ | 3-Iodo | |
| 2-19 | CH₂—C₈H₄ | Me | (CH₂)₂ | — | |
| 2-20 | CH₂—C₆H₄ | Me | (CH₂)₂ | — | |
| 2-21 | CH₂—C₆H₅ | Et | (CH₂)₂ | — | |
| 2-22 | COH(CH₃)₂ | Me | (CH₂)₂ | — | Oil |
| 2-23 | CF(CH₃)₂ | Me | (CH₂)₂ | 3-Cl | Oil |
| 2-24 | CH₂CH(CH₃)₂ | Me | (CH₂)₂ | 3,5-Me₂ | |
| 2-25 | CH₂CH(CH₃)₂ | Me | (CH₂)₂ | — | |
| 2-26 | CH₂CH(CH₃)₂ | Me | (CH₂)₂ | 3-Me | |
| 2-27 | CH₂CH(CH₃)₂ | Me | (CH₂)₂ | 3-Iodo | |
| 2-28 | CH₂CH(CH₃)₂ | Et | (CH₂)₂ | 3,5-Me₂ | |
| 2-29 | CH₂CH(CH₃)₂ | Et | (CH₂)₂ | — | |
| 2-30 | CH₂CH(CH₃)₂ | Et | (CH₂)₂ | 3-Me | |
| 2-31 | CH(CH₃)C₂H₅ | Me | (CH₂)₂ | — | |
| 2-32 | CH(CH₃)C₂H₅ | Et | (CH₂)₂ | — | |
| 2-33 | CH(CH₃)C₂H₅ | Et | (CH₂)₂ | 3-Me | |
| 2-34 | CBr(CH₃)₂ | Me | (CH₂)₂ | — | Oil |
| 2-35 | C(CH₃)₂OCH₃ | Me | (CH₂)₂ | — | Oil |
| 2-36 | CCl(CH₃)₂ | Me | (CH₂)₂ | — | Oil |
| 2-37 | CH(CH₃)₂ | Me | (CH₂)₂ | 3-Cl | Oil |
| 2-38 | i-Pr | n-Pr | (CH₂)₂ | — | Oil |
| 2-39 | i-Pr | n-Pr | (CH₂)₂ | 3-Me | |
| 2-40 | i-Pr | i-Pr | (CH₂)₂ | 3,5-Me₂ | |
| 2-41 | CFC(CH₃)₂ | i-Pr | (CH₂)₂ | 3,5-Me₂ | Oil |
| 2-42 | i-Pr | CF₃ | (CH₂)₂ | (CH₂)₂ | |
| 2-43 | CF(CH₃)₂ | CF₃ | (CH₂)₂ | — | |
| 2-44 | i-Pr | CF₃ | (CH₂)₂ | 3-Iodo | |
| 2-45 | CF(CH₃)₂ | CF₃ | (CH₂)₂ | 3-F | |
| 2-46 | i-Pr | CF₂CF₃ | (CH₂)₂ | — | |
| 2-47 | CF(CH₃)₂ | CF₂CF₃ | (CH₂)₂ | — | |
| 2-48 | CH(CH₃)C₂H₅ | CF₂CHF₂ | (CH₂)₂ | | |
| 2-49 | i-Pr | CH₂CCl₃ | (CH₂)₂ | — | |
| 2-50 | CH₂CH(CH₃)₂ | i-Pr | (CH₂)₂ | — | |
| 2-51 | i-Pr | Et | (CH₂)₂ | — | Oil |
| 2-52 | i-Pr | Et | (CH₂)₂ | 4-Cl | Oil |
| 2-53 | i-Pr | Et | (CH₂)₂ | 3,5-Me₂ | Oil |
| 2-54 | i-Pr | Et | (CH₂)₂ | 3,4-Cl₂ | Oil |

TABLE 2-continued

Compounds of the formula (Ia)

(Ia)

$$\text{H}_2\text{N}-\underset{\text{N}}{\overset{\text{N}}{\bigcirc}}-\text{NH}-\underset{\overset{|}{\text{R}^5}}{\text{CH}}-\text{A}-\text{C}_6\text{H}_4(\text{X})_n \quad ; \quad \text{R}^1\text{ on triazine}$$

| No. | R¹ | R⁵ | A | (X)ₙ | Phys. Dat. |
|---|---|---|---|---|---|
| 2-55 | i-Pr | Et | (CH₂)₂ | 3-CF₃ | Oil |
| 2-56 | i-Pr | Et | (CH₂)₂ | 3-CH₃ | |
| 2-57 | CF(CH₃)₂ | Et | (CH₂)₂ | 4-Cl | Oil |
| 2-58 | CF(CH₃)₂ | Et | (CH₂)₂ | 3,4-Cl₂ | |
| 2-59 | CF(CH₃)₂ | Et | (CH₂)₂ | 3-CF₃ | |
| 2-60 | CF(CH₃)₂ | Et | (CH₂)₂ | 3-CH₃ | |
| 2-61 | CHCH₃C₂H₅ | Et | (CH₂)₂ | — | |
| 2-62 | CH₂CH(CH₃)₂ | Et | (CH₂)₂ | — | |
| 2-63 | CF₂CHF₂ | Et | (CH₂)₂ | — | Oil |
| 2-64 | i-Pr | i-Pr | (CH₂)₂ | — | |
| 2-65 | CF(CH₃)₂ | i-Pr | (CH₂)₂ | — | |
| 2-66 | i-Pr | i-Pr | (CH₂)₂ | 3-Me | |
| 2-67 | CF(CH₃)₂ | i-Pr | (CH₂)₂ | 3-Me | |
| 2-68 | CH₂CH(CH₃)₂ | i-Pr | (CH₂)₂ | — | |
| 2-69 | i-Pr | Me | CH(CH₃)CH₂ | — | Oil |
| 2-70 | CF(CH₃)₂ | Me | CH(CH₃)CH₂ | — | Oil |
| 2-70a | CF(CH₃)₂ | Me | CH(CH₃)CH₂ | 3-F | Oil |
| 2-71 | i-Pr | Me | CH(CH₃)CH₂ | 3-CF₃ | Oil |
| 2-72 | i-Pr | Me | CH(CH₃)CH₂ | 4-Me | Oil |
| 2-73 | CF(CH₃)₂ | Me | CH(CH₃)CH₂ | 3-CF₃ | Oil |
| 2-74 | CF(CH₃)₂ | Me | CH(CH₃)CH₂ | 4-Me | Oil |
| 2-75 | CF(CH₃)₂ | Me | CH(CH₃)CH₂ | 3-Me | Oil |
| 2-76 | i-Pr | Me | CH(CH₃)CH₂ | 3-Me | Oil |
| 2-77 | CF(CH₃)₂ | Me | CH(CH₃)CH₂ | 3,5-Me₂ | Oil |
| 2-78 | C(OH)(CH₃)₂ | Me | CH₂ | — | Oil |
| 2-79 | CFC(CH₃)₂ | Et | CH₂ | 3,5-Me₂ | |
| 2-80 | i-Pr | Me | CH₂ | 3,5-Me₂ | Oil |
| 2-81 | i-Pr | Me | CH₂ | — | Oil |
| 2-82 | CF(CH₃)₂ | Et | CH₂ | — | |
| 2-83 | i-Pr | Me | CH₂ | 2,4-Me₂ | Oil |
| 2-84 | CCl(CH₃)₂ | Me | CH₂ | — | Oil |
| 2-85 | CF(CH₃)₂ | Me | CH₂ | 2,4-Me₂ | Oil |
| 2-86 | CF(CH₃)₂ | Me | CH₂ | 2-Me | |
| 2-87 | i-Pr | Me | CH₂ | 2-Me | |
| 2-88 | CF(CH₃)₂ | Me | CH₂ | 2,3-Me₂-4-OCH₃ | |
| 2-89 | i-Pr | Me | CH₂ | 2,3-Me₂-4-OCH₃ | |
| 2-90 | CF(CH₃)₂ | Me | (CH₂)₂ | 3-NH₂ | |
| 2-91 | CF(CH₃)₂ | Et | (CH₂)₂ | 3-NH₂ | |
| 2-92 | CF(CH₃)₂ | Me | (CH₂)₂ | 3-NHCOCH₃ | |
| 2-93 | CF(CH₃)₂ | Et | (CH₂)₂ | 3-NHCOCH₃ | |
| 2-94 | CF(CH₃)₂ | Me | (CH₂)₂ | 3-NH—COC₆H₅ | |
| 2-95 | CF(CH₃)₂ | Et | (CH₂)₂ | 3-NH—COC₆H₅ | |
| 2-96 | CF(CH₃)₂ | Me | (CH₂)₂ | 3-NH—CO₂CH₃ | |
| 2-97 | CF(CH₃)₂ | Et | (CH₂)₂ | 3-NH—CO₂CH₃ | |
| 2-98 | CF(CH₃)₂ | Me | (CH₂)₂ | 3-NH—CO₂C₂H₅ | |
| 2-99 | CF(CH₃)₂ | Et | (CH₂)₂ | 3-NH—CO₂C₂H₅ | |
| 2-100 | CF(CH₃)₂ | Me | (CH₂)₂ | 3-NH—COCCl₃ | |
| 2-101 | CF(CH₃)₂ | Et | (CH₂)₂ | 3-NH—COCCl₃ | |
| 2-102 | CF(CH₃)₂ | Me | (CH₂)₂ | 3-NHMe | |
| 2-103 | CF(CH₃)₂ | Et | (CH₂)₂ | 3-NHMe | |
| 2-104 | CF(CH₃)₂ | Me | (CH₂)₂ | 3-NMe₂ | |
| 2-105 | CF(CH₃)₂ | Et | (CH₂)₂ | 3-NMe₂ | |
| 2-106 | i-Pr | Me | (CH₂)₂ | 3-NH₂ | |
| 2-107 | i-Pr | Et | (CH₂)₂ | 3-NH₂ | |
| 2-108 | i-Pr | Me | (CH₂)₂ | 3-NHCOCH₃ | |
| 2-109 | i-Pr | Et | (CH₂)₂ | 3-NHCOCH₃ | |
| 2-110 | i-Pr | Me | (CH₂)₂ | 3-NHCO₂CH₃ | |
| 2-111 | i-Pr | Et | (CH₂)₂ | 3-NHCO₂CH₃ | |
| 2-112 | i-Pr | Me | (CH₂)₂ | NHMe | |
| 2-113 | i-Pr | Et | (CH₂)₂ | NHMe | |
| 2-114 | i-Pr | Me | (CH₂)₂ | NHEt | |
| 2-115 | CF(CH₃)₂ | Me | (CH₂)₂ | OCH₂C₆H₅ | |
| 2-116 | CF(CH₃)₂ | Et | (CH₂)₂ | OCH₂C₆H₅ | |
| 2-117 | CF(CH₃)₂ | Me | (CH₂)₂ | OH | |

TABLE 2-continued

Compounds of the formula (Ia)

$$\text{(Ia)}$$

Structure: 2,4-diamino-1,3,5-triazine with R¹ at position 6, H₂N at position 2, and NH—CH(R⁵)—A—phenyl(X)ₙ at position 4.

| No. | R¹ | R⁵ | A | (X)ₙ | Phys. Dat. |
|---|---|---|---|---|---|
| 2-118 | CF(CH₃)₂ | Et | (CH₂)₂ | OH | |
| 2-119 | CF(CH₃)₂ | Me | (CH₂)₂ | OCOCH₃ | |
| 2-120 | CF(CH₃)₂ | Et | (CH₂)₂ | OCOCH₃ | |
| 2-121 | CF(CH₃)₂ | Me | (CH₂)₂ | OCO₂CH₃ | |
| 2-122 | CF(CH₃)₂ | Et | (CH₂)₂ | OCO₂CH₃ | |
| 2-123 | CF(CH₃)₂ | Me | (CH₂)₂ | OCOC₆H₅ | |
| 2-124 | CF(CH₃)₂ | Et | (CH₂)₂ | OCOC₆H₅ | |
| 2-125 | CF(CH₃)₂ | Me | (CH₂)₂ | OCONMe₂ | |
| 2-126 | CF(CH₃)₂ | Et | (CH₂)₂ | OCONMe₂ | |
| 2-127 | CF(CH₃)₂ | Me | (CH₂)₂ | OCOCl₃ | |
| 2-128 | i-Pr | Me | (CH₂)₂ | OCH₂C₆H₅ | |
| 2-129 | i-Pr | Et | (CH₂)₂ | OCH₂C₆H₅ | |
| 2-130 | i-Pr | Me | (CH₂)₂ | OH | |
| 2-131 | i-Pr | Et | (CH₂)₂ | OH | |
| 2-132 | i-Pr | Me | (CH₂)₂ | OCOCH₃ | |
| 2-133 | i-Pr | Et | (CH₂)₂ | OCOCH₃ | |
| 2-134 | i-Pr | Me | (CH₂)₂ | OCO₂CH₃ | |
| 2-135 | i-Pr | Et | (CH₂)₂ | OCO₂CH₃ | |
| 2-136 | i-Pr | Me | (CH₂)₂ | OCOC₆H₅ | |
| 2-137 | i-Pr | Et | (CH₂)₂ | OCOC₆H₅ | |
| 2-138 | i-Pr | Me | (CH₂)₂ | OCONMe₂ | |
| 2-139 | i-Pr | Et | (CH₂)₂ | OCONMe₂ | |
| 2-140 | i-Pr | Me | (CH₂)₂ | OCOCCl₃ | |

B. FORMULATION EXAMPLES a) A dusting composition is obtained by mixing 10 parts by weight of a compound of the formula (I) and 90 parts by weight of talc as inert substance and comminuting the mixture in a hammer mill.

b) A readily water-dispersible, wettable powder is obtained by mixing 25 parts by weight of a compound of the formula (I), 64 parts by weight of kaolin-containing quartz as inert substance, 10 parts by weight of potassium ligno-sulfonate and 1 part by weight of sodium oleoylmethyltaurate as wetting agent and dispersant and grinding the mixture in a pinned disc mill.

c) A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255 to over 277° C.) and grinding the mixture in a friction ball mill to a fineness of less than 5 microns.

d) An emulsifiable concentrate is obtained from 15 parts by weight of a compound of the formula (I), 75 parts by weight of cyclohexanone as solvent and 10 parts by weight of ethoxylated nonylphenol as emulsifier.

e) Water-dispersible granules are obtained by mixing 75 parts by weight of a compound of the formula (I),
10 " of calcium lignosulfonate,
5 " sodium laurylsulfate,
3 " polyvinyl alcohol and
7 " kaolin, grinding in a pinned disc mill and granulating the powder in a fluidized bed by spraying on water as granulating fluid.

f) Water-dispersible granules are also obtained by homogenizing and precomminuting 25 parts by weight of a compound of the formula (I),
5 " of sodium 2,2'-dinaphthylmethane-6,6'-disulfonate
2 " of sodium oleoylmethyltaurate,
1 part by weight of polyvinyl alcohol,
17 parts by weight of calcium carbonate and
50 " of water in a colloid mill, then grinding in a bead mill and atomizing and drying the suspension thus obtained in a spray tower by means of a single-substance nozzle.

C. BIOLOGICAL EXAMPLES

1. Weed Action Pre-Emergence

Seeds or pieces of rhizome or mono- and dicotyledonous weed plants are placed in sandy loam soil in plastic pots and covered with earth. The compounds according to the invention formulated in the form of wettable powders or emulsion concentrates are then applied to the surface of the covering earth in various doses as an aqueous suspension or emulsion having a water application rate of the equivalent of 600 to 800 l/ha.

After treatment, the pots are placed in a greenhouse and kept under good growth conditions for the weeds. The visual assessment of plant and emergence damage is carried out after the emergence of the test plants after a test period of 3 to 4 weeks in comparison with untreated controls. As the test results show, the compounds according to the invention have a good herbicidal pre-emergence activity against a broad spectrum of weed grasses and weeds. For example, Examples Nos. 1, 2, 3, 4, 6, 11, 37, 38, 39, 40, 41, 43, 48, 49, 55, 91, 99, 106, 2-22, 2-23, 2-34, 2-35, 2-36, 2-37, 2-38, 2-51, 2-69, 2-70 and 2-70a (see Table 1 and 2) show very good herbicidal action in the test against harmful plants, such as *Stellaria media, Lolium multiflorum, Matricaria inodora, Echinochloa crus-galli, Sinapis alba* and *Avena sativa*, pre-emergence at an application rate of 1.25 kg or less of active substance per hectare.

2. Weed Action Post-Emergence

Seeds or pieces or rhizome of mono- and dicotyledonous weeds are placed in sandy loam soil in plastic pots, covered with earth and raised in a greenhouse under good growth conditions. Three weeks after sowing, the test plants are treated in the three-leaf stage.

The compounds according to the invention formulated as wettable powders or as emulsion concentrates are sprayed onto the green parts of the plants in various doses using a water application rate of the equivalent of 600 to 800 I/ha. After a standing time of about 3 to 4 weeks of the test plants in the greenhouse under optimum growth conditions, the action of the preparations is assessed visually in comparison with untreated controls. Post-emergence, the compositions according to the invention have a good herbicidal activity against a broad spectrum of economically important weed grasses and broad-leaved weeds. For example, Examples Nos. 1, 2, 3, 4, 5, 37, 38, 39, 40, 41, 43, 48, 49, 99, 106, 2-23, 2-34, 2-36, 2-38, 2-51, 2-69, 2-70 and 2-70a (see Tables 1 and 2) show a good herbicidal action in the test against harmful plants such as *Sinapis alba, Echinochloa crus-galli, Lolium multiflorum, Stellaria media, Matricaria inodora, Cyperus iria* and *Avena sativa* post-emergence at an application rate of 1.25 kg or less active substance per hectare.

3. Action on Harmful Plants in Rice

Transplanted and sown rice as well as typical rice weeds and weed grasses are raised in closed plastic pots in a greenhouse up to the three-leaf stage (Echinochloa 1.5 leaf) under paddy rice conditions (flooding height of the water: 2–3 cm). The treatment with the compounds according to the invention is then carried out. To do this, the formulated active compounds are suspended, dissolved or emulsified in water and applied in various doses to the flooding water of the test plants by means of watering. After treatment carried out in this manner, the test plants are placed in a greenhouse under optimum growth conditions and kept in this way during the entire test period.

Approximately three weeks after application, evaluation is carried out by means of visual assessment of the plant damage in comparison with untreated controls. The compounds according to the invention show very good herbicidal action against harmful plants. For example, the compounds of Examples Nos 1, 2, 4, 6, 11, 38, 39, 43, 49, 99, 2-35, 2-36, 2-37, 2-38, 2-51 and 2-70 (see Tables 1 and 2) show very good herbicidal action in the test against harmful plants which are typical of rice crops, such as, for example, *Cyperus monti, Echinochloa crus-galli* and *Sagittaria pygmaea*.

4. Crop Plant Tolerability

In further tests in a greenhouse, seeds of a relatively large number of crop plants and weeds are placed in sandy loam soil and covered with earth. Some of the pots are immediately treated as described under Section 1, the remainder are placed in the greenhouse until the plants have developed two to three adult leaves and then sprayed with the substances of the formula (I) according to the invention at different doses as described in Section 2. Four to five weeks after application and standing time in the greenhouse, it is found by means of visual assessment that the compounds according to the invention leave crops having two seed leaves such as, for example, soybeans, cotton, rape, sugar beet and potatoes undamaged pre-emergence and post-emergence even at high active compound doses. Some substances moreover protect graminaceous crops such as, for example, barley, wheat, rye, sorghum, corn or rice. The compounds of the formula (I) in some cases show high selectivity and are therefore suitable for the control of undesired vegetation in agricultural crops.

We claim:

1. A compound of the formula (I) or its salts

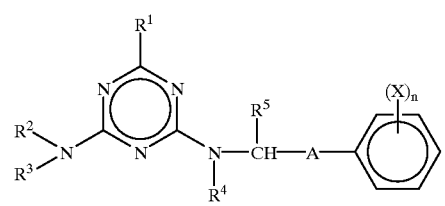

$R^1$ is $(C_1-C_6)$alkyl, which is unsubstituted or substituted by one or more radicals from the group consisting of halogen, $(C_1-C_4)$alkoxy, $(C_1-C_4)$alkylthio, $(C_1-C_4)$alkylsulfonyl, $(C_3-C_9)$cycloalkyl, which is unsubstituted or substituted by one or more radicals from the group consisting of halogen, $(C_1-C_4)$alkyl, $(C_1-C_4)$haloalkyl, $(C_1-C_4)$alkoxy and $(C_1-C_4)$haloalkoxy, and phenyl which is unsubstituted or substituted by one or more radicals from the group consisting of halogen, $(C_1-C_4)$alkyl and $(C_1-C_4)$haloalkyl, $(C_1-C_4)$alkoxy, $(C_1-C_4)$haloalkoxy, $(C_1-C_4)$alkylthio, amino, mono- and di[$(C_1-C_4)$alkyl]amino, $(C_1-C_4)$alkanoyl-amino, benzoylamino, nitro, cyano, [$(C_1-C_4)$alkyl]carbonyl, formyl, carbamoyl, mono- and di-[$(C_1-C_4)$alkyl]aminocarbonyl and $(C_1-C_4)$alkylsulfonyl, and heterocyclyl having 3 to 6 ring atoms and 1 hetero ring atom from the group consisting of N, O and S, the ring being unsubstituted or substituted by one or more radicals from the group consisting of halogen, $(C_1-C_4)$alkyl and oxo, or phenyl which is unsubstituted or substituted by one or more radicals from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, aminocarbonyl, $(C_1-C_4)$alkylaminocarbonyl, phenoxy-$(C_1-C_4)$alkyl, phenyl-$(C_1-C_4)$alkyl, heterocyclyl, heterocyclylamino, heterocyclyloxy, heterocyclylthio, or one of the last-mentioned 16 radicals, which is substituted in the acyclic moiety or, in the cyclic moiety by one or more radicals from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl, $(C_1-C_4)$alkoxy, heterocyclyl in the radicals in each case containing 3 to 6 ring atoms and 1 hetero ring atom selected from the group consisting of N, O and S, $R^2$ and $R^3$ each independently of one another are hydrogen, amino or alkylamino or dialkylamino, each having 1 to 4 carbon atoms in the alkyl radical, an acyclic or cyclic hydrocarbon radical or hydrocarbon-oxy radical, each having 1 to 6 carbon atoms, or a heterocyclyl radical, heterocyclyloxy radical or heterocyclylamino radical each having 3 to 6 ring atoms and 1 hetero ring atom selected from the group consisting of N, O and S, each of the five last mentioned radicals being unsubstituted or substituted by one or more radicals from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy]carbonyl, $[(C_1-C_4)$alkyl]carbonyl, formyl, carbamoyl, mono- and di-$[(C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, or an acyl radical or $R^2$ and $R^3$ together with the nitrogen atom of the group $NR^2R^3$ are a heterocyclic radical selected from the group consisting of piperid-1-yl and morpholin-4-yl, the radicals being unsubstituted or substituted by one or more radicals from the group consisting of halogen, $(C_1-C_4)$alkyl and oxo, $R^4$ is hydrogen, amino, alkylamino or dialkylamino each having 1 to 6 carbon atoms in the alkyl radical, an acyclic or cyclic hydrocarbon radical or hydrocarbon-oxy radical each having 1 to 6 carbon atoms or a heterocyclyl radical, heterocyclyloxy radical or heterocyclylamino radical each having 3 to 6 ring atoms and 1 hetero ring atom selected from the group consisting of N, O and S, each of the five last mentioned radicals being unsubstituted or substituted by one or more radicals from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy]carbonyl, $[(C_1-C_4)$alkyl]carbonyl, formyl, carbamoyl, mono- and di-$[(C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, or an acyl radical, $R^5$ is hydrogen, halogen $(C_1-C_6)$alkyl, $(C_1-C_6)$haloalkyl or $(C_3-C_6)$cycloalkyl, A is a divalent radical of the formula $A^2$, $A^3$ or $A^4$

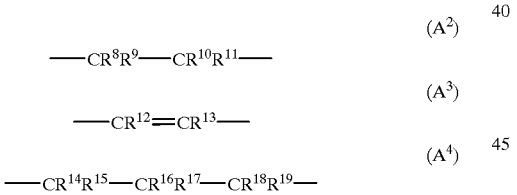

$R^8, R^9, R^{10}, R^{11}, R^{12}, R^{13}, R^{14}, R^{15}, R^{16}, R^{17}, R^{18}$ and $R^{19}$ each independently of one another are hydrogen, halogen, $(C_1-C_9)$alkyl, $(C_2-C_6)$alkenyl, $(C_2-C_6)$alkynyl, $(C_3-C_9)$cycloalkyl, $(C_3-C_9)$cycloalkenyl, phenyl, heterocyclyl having 3 to 6 ring atoms and 1 hetero ring atom selected from the group consisting of N, O and S, each of the last mentioned 7 radicals being unsubstituted or substituted by one or more radicals from the group consisting of halogen, $(C_1-C_4)$alkoxy, $(C_1-C_4)$haloalkoxy, $(C_1-C_4)$alkylthio, amino, mono- and di$[(C_1-C_4)$alkyl]amino, $(C_1-C_4)$alkanoylamino, benzoylamino, nitro, cyano, $[(C_1-C_4)$alkyl]carbonyl, formyl, carbamoyl, mono- and di-$[(C_1-C_4)$alkyl]aminocarbonyl, $(C_1-C_4)$alkylsulfonyl and, in the case of cyclic radicals, also $(C_1-C_4)$alkyl and $(C_1-C_4)$haloalkyl, $(X)_n$ is n substituents X and in this case X in each case independently of one another is halogen, hydroxyl, amino, nitro, formyl, carboxyl, cyano, thiocyanato, $(C_1-C_4)$alkyl, cyano-$(C_1-C_4)$alkyl, $(C_1-C_4)$alkoxy, $(C_1-C_4)$alkylamino, di-$[(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di-$[(C_1-C_4)$alkyl]amino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 9 ring members, the cyclic groups in the last mentioned 3 radicals being unsubstituted or substituted by one or more radicals from the group consisting of $(C_1-C_4)$alkyl, halogen and cyano or phenyl, phenoxy, phenylcarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, aminocarbonyl, $(C_1-C_4)$alkylaminocarbonyl, phenoxy-$(C_1-C_4)$alkyl, phenyl-$(C_1-C_4)$alkyl, heterocyclyl, heterocyclylamino, heterocyclyloxy, heterocyclylthio or one of the last mentioned 16 radicals, which is substituted in the acyclic moiety or in the cyclic moiety by one or more radicals from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl, $(C_1-C_4)$alkoxy, heterocyclyl in the radicals in each case containing 3 to 6 ring atoms and 1 hetero ring atom selected from the group consisting of N, O and S, or two adjacent radicals X together are a fused cyclic system having 4 to 6 ring atoms, which is carbocyclic or contains hetero ring atoms selected from the group consisting of O, S and N and which is unsubstituted or substituted by one or more radicals from the group consisting of halogen, $(C_1-C_4)$alkyl and oxo, n is 0, 1, 2, 3, 4 or 5.

2. A compound of the formula (I) or its salts as claimed in claim 1, wherein $R^1$ is $(C_1-C_6)$alkyl, which is unsubstituted or substituted by one or more radicals from the group consisting of halogen, cyano, nitro, thiocyanato, $(C_1-C_4)$alkoxy, $(C_1-C_4)$alkylthio, $(C_1-C_4)$alkylsulfinyl, $(C_1-C_4)$alkylsulfonyl, $(C_2-C_4)$alkenyl, $(C_2-C_4)$alkynyl, $(C_3-C_9)$cycloalkyl, which is unsubstituted or substituted by one or more radicals from the group consisting of halogen, $(C_1-C_4)$alkyl, $(C_1-C_4)$haloalkyl, $(C_1-C_4)$alkoxy and $(C_1-C_4)$haloalkoxy, and phenyl which is unsubstituted or substituted by one or more radicals from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, nitro, cyano, $[(C_1-C_2)$alkyl]carbonyl, formyl, carbamoyl, mono- and di-$[(C_1-C_2)$alkyl]aminocarbonyl and $(C_1-C_4)$alkylsulfonyl, or phenyl which is unsubstituted or substituted by one or more radicals from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, nitro, cyano, $[(C_1-C_2)$alkyl]carbonyl, formyl, carbamoyl, mono- and di-$[(C_1-C_2)$alkyl]aminocarbonyl and $(C_1-C_4)$alkylsulfonyl, $R^2$ and $R^3$ independently of one another are hydrogen, amino, formyl, $(C_1-C_4)$alkyl, cyano-$(C_1-C_4)$alkyl, $(C_1-C_4)$alkylamino, di-$[(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo$(C_1-C_4)$alkoxy-$(C_1-C_4)$alkyl, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di-$[(C_1-C_4)$alkyl]amino-$(C_1-C_4)$alkyl, $(C_3-C_9)$cycloalkylamino-$(C_1-C_4)$alkyl, $(C_3-C_9)$cycloalkyl, the cyclic groups in the last-mentioned two radicals being unsubstituted or substituted by one or more radicals from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, aminocarbonyl, $(C_1-C_4)$alkylaminocarbonyl, phenoxy-$(C_1-C_4)$alkyl, phenyl-$(C_1-C_4)$alkyl, or one of the last-mentioned 12 radicals, which is substituted in the acyclic moiety or in the cyclic moiety by one or more radicals from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl, or $(C_1-C_4)$alkoxy, or $R^2$ and $R^3$ together with the nitrogen atom of the group $NR^2R^3$ are a heterocyclic radical selected from the group consisting of piperid-1-yl and morpholin-4-yl, the radicals being unsubstituted or substituted by one or more radicals from the group consisting of halogen, $(C_1-C_4)$alkyl and oxo, $R^4$ is hydrogen, amino, formyl, $(C_1-C_4)$alkyl, cyano-$(C_1-C_4)$alkyl, $(C_1-C_4)$alkylamino, di-$[(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo$(C_1-C_4)$-alkoxy-$(C_1-C_4)$alkyl, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di-$[(C_1-C_4)$alkyl]amino-$(C_1-C_4)$alkyl, $(C_3-C_9)$cycloalkylamino-$(C_1-C_4)$alkyl, $(C_3-C_9)$cycloalkyl, the cyclic groups in the last mentioned 7 radicals are unsubstituted or substituted by one or more radicals selected from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, aminocarbonyl, $(C_1-C_4)$alkylaminocarbonyl, phenoxy-$(C_1-C_4)$alkyl, and phenyl-$(C_1-C_4)$alkyl, or one of the last mentioned 12 radicals which is substituted in the acyclic moiety or in the cyclic moiety by one or more radicals from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl, or $(C_1-C_4)$alkoxy, $R^5$ is hydrogen, $(C_1-C_4)$alkyl, $(C_1-C_4)$haloalkyl or $(C_3-C_6)$cycloalkyl, A is a divalent radical of said formula $A^2$, $A^3$ or $A^4$,

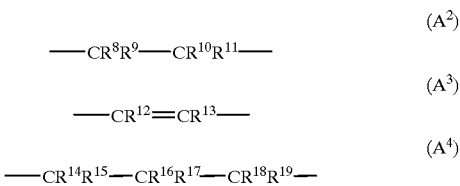

$R^8, R^9, R^{10}, R^{11}, R^{12}, R^{13}, R^{14}, R^{15}, R^{16}, R^{17}, R^{18}$ and $R^{19}$ each independently of one another are hydrogen, halogen, $(C_1-C_8)$alkyl, $(C_2-C_6)$alkenyl, $(C_2-C_6)$alkynyl, $(C_3-C_9)$cycloalkyl, $(C_3-C_9)$cycloalkenyl, phenyl, each of the last mentioned 6 radicals being unsubstituted or substituted by one or more radicals from the group consisting of halogen, $(C_1-C_4)$alkoxy, $(C_1-C_4)$haloalkoxy, $(C_1-C_4)$alkylthio, amino, mono- and di$[(C_1-C_4)$alkyl]amino, $(C_1-C_4)$alkanoylamino, benzoylamino, nitro, cyano, $[(C_1-C_4)$alkyl]carbonyl, formyl, carbamoyl, mono- and di-$[(C_1-C_4)$alkyl]aminocarbonyl, $(C_1-C_4)$alkylsulfonyl and, in the case of cyclic radicals, also $(C_1-C_4)$alkyl and $(C_1-C_4)$haloalkyl, $(X)_n$ is n substituents X and in this case X in each case independently of one another is halogen, hydroxyl, amino, nitro, formyl, carboxyl, cyano, thiocyanato, $(C_1-C_4)$alkyl, cyano-$(C_1-C_4)$alkyl, $(C_1-C_4)$alkoxy, $(C_1-C_4)$alkylamino, di-$[(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di-$[(C_1-C_4)$alkyl]amino-$(C_1-C_4)$alkyl, $(C_3-C_9)$cycloalkylamino-$(C_1-C_4)$alkyl, $(C_3-C_9)$cycloalkyl, where the cyclic groups in the last mentioned 2 radicals being unsubstituted or substituted by one or more radicals from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, aminocarbonyl, $(C_1-C_4)$alkylaminocarbonyl, phenoxy-$(C_1-C_4)$alkyl, or phenyl-$(C_1-C_4)$alkyl, or one of the last mentioned 12 radicals, which is substituted in the acyclic moiety or in the cyclic moiety by one or more radicals from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl, or $(C_1-C_4)$alkoxy, n is 0, 1, 2, 3, 4 or 5.

3. A compound of the formula (I) or its salts as claimed in claim 1, wherein $R^2$ and $R^3$ together with the nitrogen atom of the group $NR^2R^3$ are a heterocyclic radical selected from the group consisting of piperid-1-yl and morpholin-4-yl and said radicals are optionally substituted by one or more radicals selected from the group consisting of halogen, $(C_1-C_4)$alkyl and oxo, $R^4$ is hydrogen, amino, formyl, $(C_1-C_4)$alkyl, di-$[C_1-C_4)$alkyl]amino, $(C_1-C_4)$alkoxy-$(C_1-C_4)$alkyl, $(C_2-C_6)$alkenyl, $(C_2-C_6)$alkynyl, $(C_1-C_4)$dialkylamino-$(C_1-C_4)$alkyl, phenyl, phenoxy-$(C_1-C_4)$alkyl, phenyl-$(C_1-C_4)$alkyl, phenoxycarbonyl, phenylaminocarbonyl or one of the last mentioned five radicals, which is substituted in the phenyl moiety one to three times by radicals from the group consisting of halogen, $(C_1-C_4)$alkyl, $(C_1-C_4)$alkoxy and $(C_1-C_4)$alkoxycarbonyl, $R^5$ is hydrogen, $(C_1-C_4)$alkyl, $(C_1-C_4)$haloalkyl or $(C_3-C_6)$cycloalkyl, A is a divalent radical of said formula $A^2$, $A^3$ or $A^4$, $R^8, R^9, R^{10}, R^{11}, R^{12}, R^{13}, R^{14}, R^{15}, R^{16}, R^{17}, R^{18}$ and $R^{19}$ each independently of one another are hydrogen, halogen or $(C_1-C_4)$alkyl.

4. A compound of the formula (I) or its salts as claimed in claim 1, wherein $R^1$ is $(C_1-C_4)$haloalkyl, $R^2$ and $R^3$ are hydrogen, $R^4$ is hydrogen, $R^5$ is $(C_1-C_3)$alkyl or $(C_3-C_4)$cycloalkyl, A is —$CH_2CH_2$— or —$CH_2$—$CH_2$—$CH_3$—, X is halogen, $(C_1-C_4)$alkyl, or $(C_1-C_4)$ alkoxy; and n is 0, 1, or 2.

5. A compound of the formula (I) or its salts as claimed in claim 1, wherein $R^1$ is $(C_1-C_4)$alkyl, $(C_1-C_4)$haloalkyl, benzyl or $[C_3-C_6)$cycloalkyl]-$(C_1-C_2)$alkyl, $R^2$ and $R^3$ independently of one another are hydrogen, amino, formyl, $(C_1-C_4)$alkyl, $(C_1-C_4)$alkoxy-$(C_1-C_4)$ alkyl, $(C_2-C_6)$alkenyl, $(C_2-C_6)$alkynyl, $(C_1-C_4)$alkylamino-$(C_1-C_4)$alkyl, di-$[(C_1-C_4)$alkyl]-amino-$(C_1-C_4)$alkyl or phenyl, phenyl-$(C_1-C_4)$alkyl or phenoxycarbonyl or one of the last mentioned three radicals, which is substituted in the phenyl moiety up to three times by radicals from the group consisting of halogen, $(C_1-C_4)$alkyl, $(C_1-C_4)$alkoxy and $(C_1-C_4)$alkoxycarbonyl, or $R^2$ and $R^3$ together with the nitrogen atom of the group $NR^2R^3$ are a heterocyclic radical selected from the group consisting of piperid-1-yl and morpholin-4-yl and said radicals are optionally substituted by one or more radicals selected from consisting of halogen, $(C_1-C_4)$alkyl and oxo, $R^4$ is hydrogen, amino, formyl, $(C_1-C_4)$alkyl, di-$[C_1-C_4)$alkyl]amino, $(C_1-C_4)$alkoxy-$(C_1-C_4)$alkyl, $(C_2-C_6)$alkenyl, $(C_2-C_6)$alkynyl, $(C_1-C_4)$dialkylamino-$(C_1-C_4)$alkyl, phenyl, phenoxy-$(C_1-C_4)$alkyl, phenyl-$(C_1-C_4)$alkyl, phenoxycarbonyl, phenylaminocarbonyl or one of the last mentioned five radicals, which is substituted in the phenyl moiety one to three times by radicals from the group consisting of halogen, $(C_1-C_4)$alkyl, $(C_1-C_4)$alkoxy and $(C_1-C_4)$alkoxycarbonyl, $R^5$ is hydrogen, $(C_1-C_4)$alkyl, $(C_1-C_4)$haloalkyl or $(C_3-C_6)$cycloalkyl, A is a divalent radical of said formula $A^2$, $A^3$ or $A^4$, $R^8, R^9, R^{10}, R^{11}, R^{12}, R^{13}, R^{14}, R^{15}, R^{16}, R^{17}, R^{18}$ and $R^{19}$ each independently of one another are hydrogen, halogen or $(C_1-C_4)$alkyl, $(X)_n$ is n substituents X and in this case X in each case independently of one another is halogen, hydroxyl, $(C_1-C_4)$alkyl or $(C_1-C_4)$alkoxy.

6. A compound of the formula (I) or its salts as claimed in claim 1, wherein $R^1$ is $(C_1-C_4)$alkyl, $(C_1-C_4)$haloalkyl or $[(C_3-C_6)$cycloalkyl]methyl, $R^2$ and $R^3$ independently of one another are hydrogen, amino, formyl or $(C_1-C_4)$alkyl or $R^2$ and $R^3$ together with the nitrogen atom of the group $NR^2R^3$ are a heterocyclic radical selected from the group consisting of piperid-1-yl and morpholin-4-yl, $R^4$ is hydrogen or $(C_1-C_4)$alkyl, $R^5$ is H, $(C_1-C_4)$alkyl or $(C_1-C_4)$haloalkyl, A is a divalent radical of said formula $A^2$ or $A^3$, $R^8, R^9, R^{10}, R^{11}, R^{12}$ and $R^{13}$ each independently of one another are hydrogen or $(C_1-C_4)$alkyl, $(X)_n$ is n substituents X and in this case X in each case independently of one another is halogen, hydroxyl, $(C_1-C_4)$alkyl or $C_1-C_4)$alkoxy.

7. A process for the preparation of the compounds of the formula (I) or their salts as defined in claim 1, which comprises a) reacting a compound of the formula (II)

in which Fu is a functional group from the group consisting of carboxylic acid ester, carboxylic acid orthoester, carboxylic acid chloride, carboxamide, carboxylic anhydride and trichloromethyl, with a biguanidide of the formula (III) or an acid addition salt thereof or

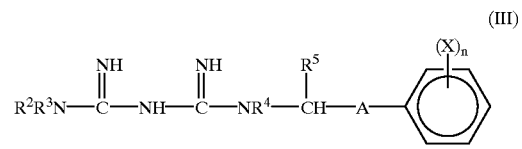

b) reacting a compound of the formula (IV)

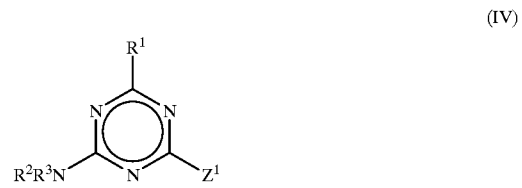

in which $Z^1$ is a replaceable radical or a leaving group with a suitable amine of the formula (V) or an acid addition salt thereof

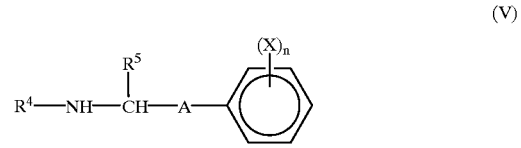

where in the formulae (II), (III), (IV) and (V) the radicals $R^1$, $R^2$, $R^3$, $R^4$, $R^5$, A and X and also n are as defined in formula (I).

8. A herbicidal or plant growth-regulating composition, which contains at least one compound of the formula (I) or its salt as defined in claim 1, and formulation aids customary in plant protection.

9. A method for the control of harmful plants or for regulating the growth of plants, which comprises applying an effective amount of at least one compound of the formula (I) or its salt as defined in claim 1 to the plants, plant seeds or the cultivation area.

* * * * *